US007872108B2

(12) United States Patent
Vodyanoy et al.

(10) Patent No.: US 7,872,108 B2
(45) Date of Patent: Jan. 18, 2011

(54) PROCESSES FOR ISOLATING PROTEON NUCLEATION CENTERS (PNCS) FROM A BIOLOGICAL SAMPLE OBTAINED FROM AN ANIMAL

(75) Inventors: Vitaly J. Vodyanoy, Auburn, AL (US); Alexandre M. Samoylov, Urbana, IL (US); Oleg M. Pustovyy, Auburn, AL (US)

(73) Assignee: Auburn University, Auburn, AL (US)

( * ) Notice: Subject to any disclaimer, the term of this patent is extended or adjusted under 35 U.S.C. 154(b) by 190 days.

(21) Appl. No.: 12/107,477

(22) Filed: Apr. 22, 2008

(65) Prior Publication Data

US 2008/0262206 A1 Oct. 23, 2008

Related U.S. Application Data

(60) Division of application No. 11/005,416, filed on Dec. 6, 2004, now abandoned, which is a continuation-in-part of application No. 10/674,750, filed on Sep. 30, 2003, now Pat. No. 7,138,255.

(60) Provisional application No. 60/415,108, filed on Sep. 30, 2002.

(51) Int. Cl.
*C07K 1/00* (2006.01)
(52) U.S. Cl. .................. 530/414; 530/350; 435/7.1; 435/91.2
(58) Field of Classification Search .............. None
See application file for complete search history.

(56) References Cited

U.S. PATENT DOCUMENTS

| 5,143,837 | A | 9/1992 | Sova et al. |
| 5,874,238 | A | 2/1999 | Potempa et al. |
| 6,036,774 | A | 3/2000 | Lieber et al. |
| 7,138,255 | B2 | 11/2006 | Vodyanoy |
| 2007/0122799 | A1 | 5/2007 | Vodyanoy et al. |
| 2007/0128642 | A1 | 6/2007 | Vodyanoy et al. |

FOREIGN PATENT DOCUMENTS

| WO | 96/37282 A1 | 11/1996 |
| WO | WO 98/53849 | 12/1998 |
| WO | WO 02/073210 | 9/2002 |

OTHER PUBLICATIONS

Houston et al., "Tramsmission of BSE by blood transfusion in sheep", The Lancet, Sep. 16, 2000, pp. 999-1000, vol. 356.
Lisiecki et al., "Syntheses of Copper nanoparticles in gelified microemulsion and in reverse micelles", Journal of Molecular Liquids, 1997, pp. 251-261, vol. 72.
Shaked et al., "Copper Binding to the PrP Isoforms: a Putative Marker of Their Conformation and Function", Journal of Virology, Sep. 2001, pp. 7872-7874, vol. 75, No. 17.
Geschwind, Michael D. (M.D., Ph.D.), et al, "Challenging the Clinical Utility of the 14-3-3 Protein for the Diagnosis of Sporadic Creutzfeldt-Jakob Disease", Arch Neurol, vol. 60, Jun. 2003, pp. 813-816.
Rahman, Qamar, et al, "Evidence That Ultrafine Titanium Dioxide Induces Micronuclei and Apoptosis in Syrian Hamster Embryo Fibroblasts", Environmental Health Perspectives, vol. 110, No. 8, Aug. 2002, pp. 797-800.
Aguzzi, A., "Prion Diseases, Blood and the Immune System: Concerns and Reality," Haematologica, 2000, pp. 3-10, vol. 85, No. 1.
Aguzzi, A., "Blood Simple Prion Diagnostics," Nature Medicine, 2001, pp. 289-290, vol. 7, No. 3, Nature Publishing Group.
Aiken III, J.D., & R.G. Finke, "A Review of Modern Transition-Metal Nanoclusters: Their Synthesis, Characterization, and Applications in Catalysis," Journal of Molecular Catalysis A: Chemical, 1999, pp. 1-44, vol. 145, Elsevier Science B.V.
Attwood, T.K., "Metals in Prion Disease," Trends in Biotechnology, 2002, p. 235, vol. 20, No. 6.
Binns et al., "Synchrotron Radiation Studies of Mass-Selected Fe Nanoclusters Deposited in Situ," Eur. Phys. J.D., 2001, pp. 189-192, vol. 16.
Brown, P., et al., "Blood Infectivity and the Prospects for a Diagnostic Screening Test in Creutzfeldt-Jakob Disease," J. Lab. Clin. Med., 2001, pp. 5-13, vol. 137, Mosby Inc.
Bush, A.I., "Metals and Neuroscience," Current Opinions in Chemical Biology, 2000, pp. 184-191, vol. 4, Elsevier Science Ltd.
Bush, A., et al., "Rapid Induction of Alzheimer A Beta Amyloid Formation by Zinc," Science, 1994, pp. 1464-1467, vol. 265, No. 5177.
Bush, A.I., "Metal Complexing Agents as Therapies for Alzheimer's Disease," Neurobiology of Aging, 2002, pp. 1031-1038, vol. 23, Elsevier Science Inc.
Campbell, A., et al., "Mechanisms by which Metals Promote Events Connected to Neurodegenerative Diseases," Brain Research Bulletin, 2001, pp. 125-132, vol. 55, No. 2, Elsevier Science Inc.
Carrel, R.W., & D.A. Lomas, "Conformational Disease," Lancet, 1997, pp. 134-138, vol. 350.
Dyson et al, Biophysical J., 2002, vol. 82, p. 824.
Gerner, C., "Biochemische Analyse Endobiontischer Strukturen aus dem Menshlichen Blut," ["Biochemical Analysis of Endobiontic Structures from Human Blood"] Curriculum Oncologicum 01, Jan. 7, 1997.
Greschwind et al, Neurology, 2002, vol. 58, p. A135.

(Continued)

Primary Examiner—Hope A Robinson
(74) Attorney, Agent, or Firm—Andrus, Sceales, Starke & Sawall, LLP

(57) ABSTRACT

Compositions and methods for the isolation and manipulation of misfolded, or partially misfolded, proteins present in blood and other biological materials are provided. In one aspect of the invention, the compositions, hereinafter termed "proteons" are comprised of misfolded proteins. Also provided are compositions and methods for the isolation and manipulation of proteon nucleation centers (PNCs) upon which the proteons of the present in blood and other biological materials form. In another aspect of the invention, the PNCs are comprised of metallic nanoclusters.

18 Claims, 5 Drawing Sheets

OTHER PUBLICATIONS

Figure 1:
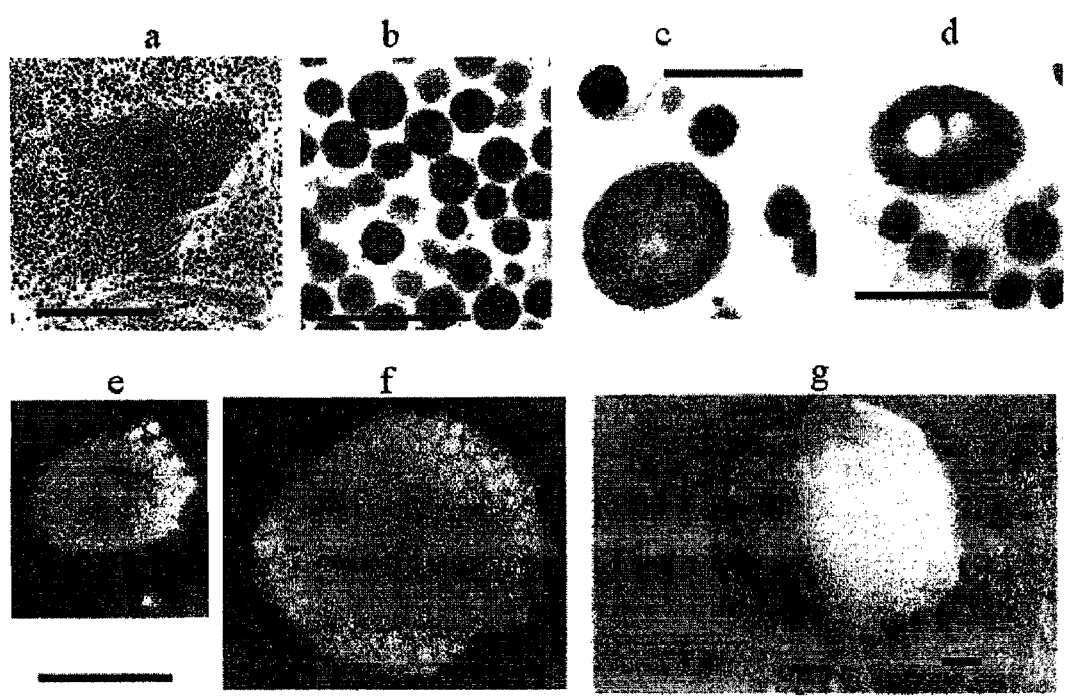

Haritani et al., "Hydrated autoclave pretreatment enhancement of prion protein immunoreactivity in formalin-fixed bovine spongiform encephalopathy-affected brain," *Acta Neuropathologica*, Jan. 1994, vol. 87, No. 1, pp. 86-90.

Harper, J.D. & P.T. Lansbury, Jr., "Models of Amyloid Seeding in Alzheimer's Disease and Scrapie: Mechanistic Truths and Physiological Consequences of the Time-Dependent Solubility of Amyloid Proteins," *Ann. Rev. Biochem.*, 1997, vol. 66, pp. 385-407, Annual Reviews Inc.

Jaikaran and Clark, *Biochimica et Biophysica Acta*, 2001, vol. 1537, pp. 179-203.

Kannan et al., J. Biol. Chem., 1988, vol. 263, pp. 13766-13773.

Krasemann et al., "Induction of antibodies against human prion proteins (PrP) by DNA-mediated immunization of PrP0/0 mice." *J Immunol Methods.*, Dec. 15, 1996, vol. 199, No. 2, p. 109-118.

Lehmann, S., "Metal Ions and Prion Diseases," *Current Opinion in Chemical Biology*, 2002, vol. 6, pp. 187-192, Elsevier Science Ltd.

Liu, C., & H. Xu, "The Metal Site as a Template for the Metalloprotein Structure Formation," *Journal of Inorganic Biochemistry*, 2002, vol. 88, pp. 77-86, Elsevier Science B.V.

Otvos, J.D., & I.M. Armitage, "Structure of the Metal Clusters in Rabbit Liver Metallothionen," *Proc. Natl. Acad. Sci. USA.*, Dec. 1980, vol. 77, No. 12, pp. 7094-7098.

Prusiner, *Science*, 1992, vol. 252, pp. 1515-1522.

Rhodes, E., et al., "Aggregation of an Amyloidogenic Fragment of Human Islet Emyloid Polypeptide," *Biochemica et Biophysica Acta*, 2000, pp. 230-238, vol. 1476, Elsevier Science B.V.

Saborio, G., et al, "Sensitive Detection of Pathological Prion Protein by Cyclic Amplification of Protein Misfolding," *Nature*, 2001, pp. 810-813, vol. 411, Macmillan Magazines Ltd.

Schluter et al., *PNAS*, 1986, vol. 83, pp. 6137-6141.

Soto, C., et al., "Cyclic Amplification of Protein Misfolding: Application to Prion-Related Disorders and Beyond," *Trends in Neurosciences*, 2002, pp. 390-394, vol. 25, No. 8, Elsevier Science Ltd.

Soto, *FEBS Letters*, 2001, vol. 498, pp. 204-207.

Thackray, A., et al, "Metal Imbalance and Compromised Antioxidant Function are Early Changes in Prion Disease," *Biochem. J.*, 2002, pp. 253-258, vol. 362.

Ursini et al, *Trends Mol. Med.*, 2001, vol. 8, pp. 370-374.

Watanabe et al., "Inhibition against heat coagulation of Ovotransferrin by Ovalbumin Dry-Heated at 120 Degrees," *C.J. Agric. Food Chem.*, Sep. 2000, vol. 48, No. 9, pp. 3965-3972.

Wetterberg et al, *Neurosci Lett.*, 2001, vol. 329, pp. 91-95.

Wille et al., *Biophysical J.*, 2002, vol. 82, p. 825.

Wille et al., *PNAS*, 2002, vol. 99, pp. 3563-3568.

Kapoor et al., "Laser-induced fragmentation and melting of cadmium and copper nanoparticles", Materials Research Bulletin, 2000, 35(13).

Makeig et al., "Response: Event-related brain dynamics-unifying brain electrophysiology", Trends in Neurosciences, Aug. 2002, 25(8):390.

Rataboul et al., "Synthesis and Characterization of Monodisperse Zinc and Zinc Oxide Nanoparticles from the Organometallic Precursor [Zn(C6H11)2]", Journal of Organometallic Chemistry, 2002, 643-644.

Rivas et al., "First Steps Towards Tailoring Fine and Ultrafine Iron Particles Using Microemulsions", IEEE Transactions on Magnetics, 1993, 29(6).

Samoylov et al., "Novel Metal Clusters Isolated from Blood are Lethal to Cancer Cells", Cells Tissues Organs, 2005, 179:115-124.

Yeadon et al., "In-situ Observations of Classical Grain Growth Mechanisms During Sintering of Copper nanoparticles on (001) Copper", Applied Physics Letters, 1997, 71(12).

PROCESSES FOR ISOLATING PROTEON NUCLEATION CENTERS (PNCS) FROM A BIOLOGICAL SAMPLE OBTAINED FROM AN ANIMAL

CROSS-REFERENCE TO RELATED APPLICATIONS

This application is a divisional application of U.S. application Ser. No. 11/005,416, filed on Dec. 6, 2004, and now abandoned; which is a continuation-in-part of U.S. patent application Ser. No. 10/674,750 filed on Sep. 30, 2003, now issued as U.S. Pat. No. 7,138,255; which claims the benefit of U.S. Provisional Application Ser. No. 60/415,108, filed on Sep. 30, 2002; which related applications are incorporated herein by reference in their entireties.

FIELD OF THE INVENTION

The present invention relates generally to compositions and methods for the isolation and manipulation of misfolded proteins and their nucleation centers.

BACKGROUND OF THE INVENTION

There are many disorders that are thought to arise from the same general mechanism based upon misfolding and aggregation of underlying proteins, including prion-related disorders, neurodegenerative diseases, and several systemic disorders. See, for example, Schluter et al. (1986) *PNAS* 83:6137-6141; Kannan et al. (1988) *J. Biol. Chem.* 263:3766-13773; Carrell and Lomas (1997) *Lancet* 350:134-138; Carrell and Gooptu (1998) *Curr. Op. Struc. Biol.* 8:799-809; Soto (2001) *FEBS Letters* 498:204-207; Jaikaran and Clark (2001) *Biochimica et Biophysica Acta* 1537:179-203; Ursini et al (2002) *Trends Mol. Med* 8:370-374; and Davis et al. (2002) *Lancet* 359:2242-2247.

One of the suggested mechanisms of protein aggregation is seeded polymerization, in which initial seeds nucleate the deposition of monomers. For example, aggregates of denatured hemoglobin called Heinz bodies were found in aged erythrocytes. See Schluter et al. (supra). Further, Kannan et al. (supra) described a protein aggregation from sickle erythrocytes that is mostly composed of globin. Particles resembling those described by Enderlein (1925) *Bakterien-Cyclogenie* (Verlag de Gruyter & Co, Berlin), were isolated from the blood of cancer patients and determined to be composed of mainly denatured hemoglobin (Gemer (1997) *Blut. Curr. Onkol.* 7:6P12).

Aggregated proteins associated with disorders are found in other biological materials, as well. For example, proteinaceous particles isolated from brain were identified as causing scrapie (Prusiner (1982) *Science* 216:136-144). Since then, these particles and their structure have represented important areas of study (Prusiner (1991) *Science* 252:1515-1522; Wille et al. (2002) *Biophysical J.* 82:825; Wille et al. (2002) *PNAS* 99:3563-3568; Geschwind et al. (2002) *Neurology* 58:A135-A135; Dyson et al. (2002) *Biophysical J.* 82:824), and methods for the sensitive detection of prion-related disorders using ultrasound have been developed. See Saborio (2001) *Nature* 411:810-813. Recently, micrometer-sized particles were identified in the cerebrospinal fluid of patients with schizophrenia (Wetterberg et al (2002) *Neurosci Lett.* 329:91-5). Accordingly, new compositions and methods for the formation, isolation, and detection of misfolded, aggregated proteins are required.

BRIEF SUMMARY OF THE INVENTION

Compositions and methods for the isolation and manipulation of misfolded, or partially misfolded, proteins present in blood and other biological materials are provided. In one aspect of the invention, the compositions, hereinafter termed "proteons," are comprised of misfolded proteins. Also provided are compositions and methods for the isolation and manipulation of proteon nucleation centers (PNCs), upon which the proteons of the present invention form. The PNCs are comprised of metallic nanoclusters.

Proteons can be visualized by microscopy of biological materials, for example fluids such as blood samples of mammals and homogenates of vegetable matter. As proteons are comprised of misfolded proteins, detection of proteons and identification of the proteins can be used to diagnose and measure progression of disease states. For example, proteons isolated and purified from blood and blood plasma lack detectable nucleic acids, but contain two major polypeptide populations with high homology to the alpha chain of hemoglobin.

Accordingly, methods for the amplification and detection of misfolded protein in a biological sample are provided. Additionally, methods for the clearance of misfolded protein from a sample of biological material are provided. The method can be manipulated by subjecting the sample to heat or pressure, or by carrying out various numbers of seeding steps. Methods for amplification include heat and pressure treatment of a sample. Likewise, subjecting a biological sample to or treating it with metal clusters increases the concentration of proteons.

While the present invention is not bound to any particular mode of action, it is believed that proteons are formed by a mechanism involving the reversible polymerization and aggregation of proteins, particularly misfolded proteins, on a nucleation center. For convenience, the nucleation centers are referred to as "proteon nucleation centers" or "PNCs."

The PNCs of the invention are unexpectedly pro-apoptotic when added to cultured animal cells. Accordingly, pro-apoptotic compositions and methods for their production are also provided herein.

BRIEF DESCRIPTION OF THE SEVERAL VIEWS OF THE DRAWING(S)

FIG. 1 shows various electron micrographs of proteons in thin sections. Transmission electron microscopy (TEM) was used to prepare electron micrographs of type 1 proteons. See FIG. 1A and FIG. 1B. Also shown are TEM of type 2 proteons. See FIG. 1C and FIG. 1D. TEM of negatively stained type 2 proteons are shown in FIG. 1E and FIG. 1F. An electron micrograph of a type 2 proteon prepared using scanning electron microscopy (SEM) is shown in FIG. 1G. Scale bars (in microns): FIG. 1A: 5; FIG. 1B-1F: 0.5; FIG. 1G: 1.

Figure 2:
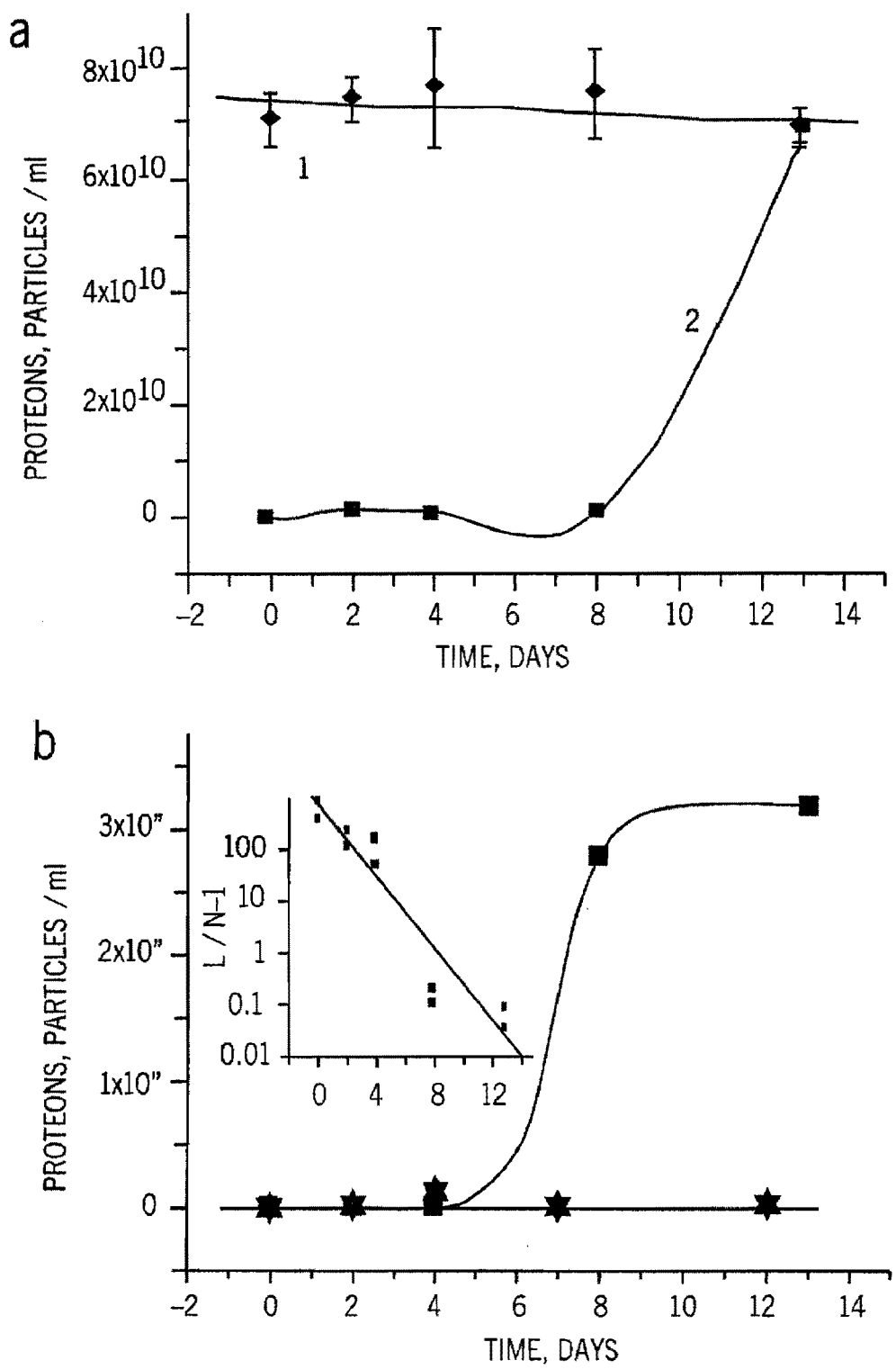
Figure 2:
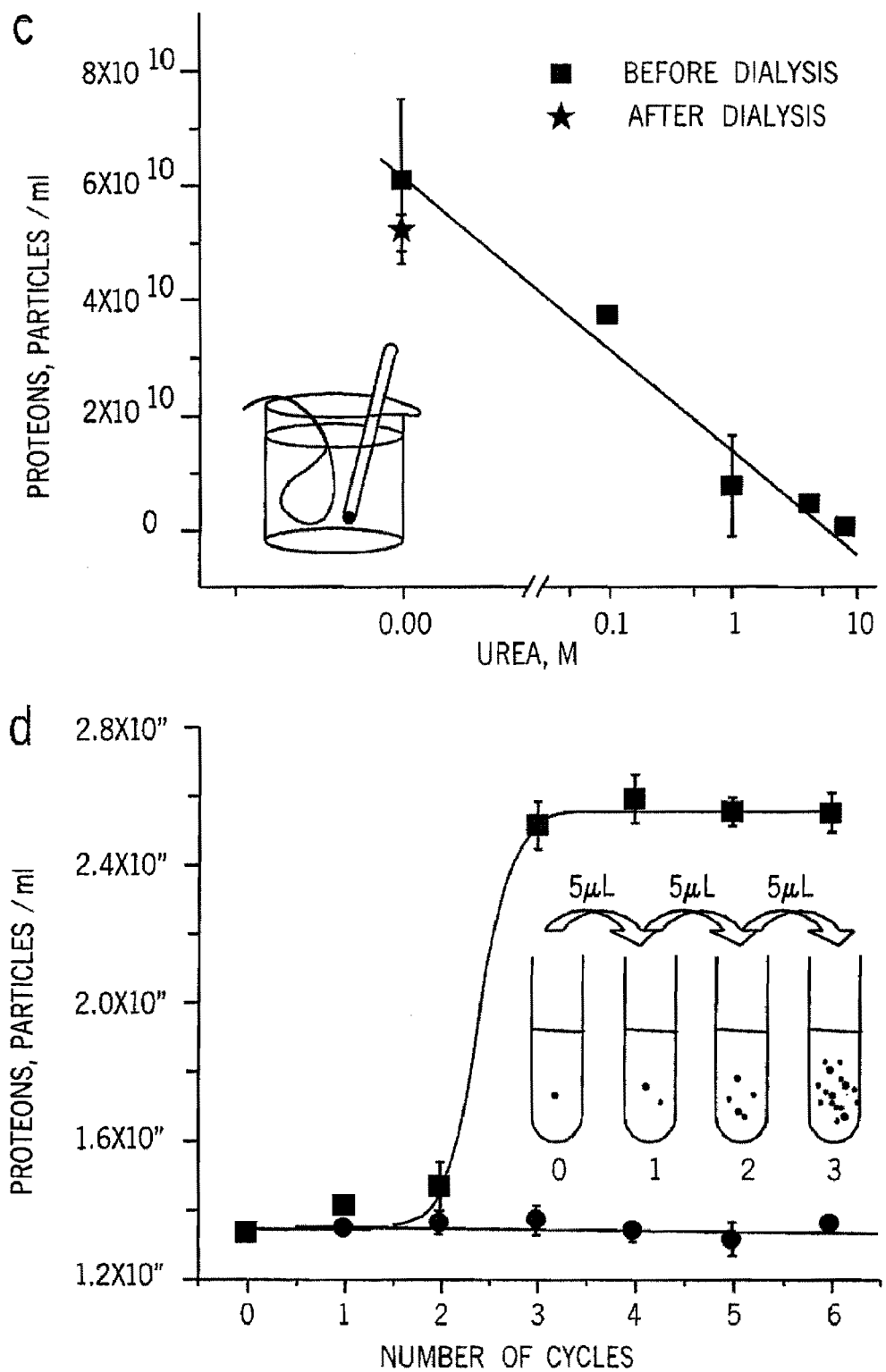

FIG. 2 shows proliferation of proteons. Proteons in purified water and blood plasma incubated at 37° C. in an atmosphere of ambient air, showing the number of proteons visible in the dark-field microscope as a function of time. See FIG. 2A. Proteons and plasma were incubated in tissue culture media. ■, ●—proteons and plasma in culture growth medium, respectively; ▲, ▼—D5648 and D6429 growth medium, respectively. The insert shows a linear fit of the experimental data to the logistic equation $Ln(L/N-1)=k(T_{1/2}-t)$, where L=maximal number of proteons, N=number of proteons at time t, and $T_{1/2}$=time when N=L/2 (Jarman, 1970). See FIG. 2B. Assembly and disassembly of proteons in the presence of urea is shown in FIG. 2C. After the proteons were assembled in the presence of urea, the urea was then removed from the suspension of proteons by dialysis. Cyclic amplification of proteons in plasma is shown in FIG. 2D. The first sample was incubated for 15 minutes at 65° C. and normal pressure. Treated samples of 5 μL were serially introduced into untreated sample and subjected to a heat cycle, up to 6 cycles.

Figure 3:
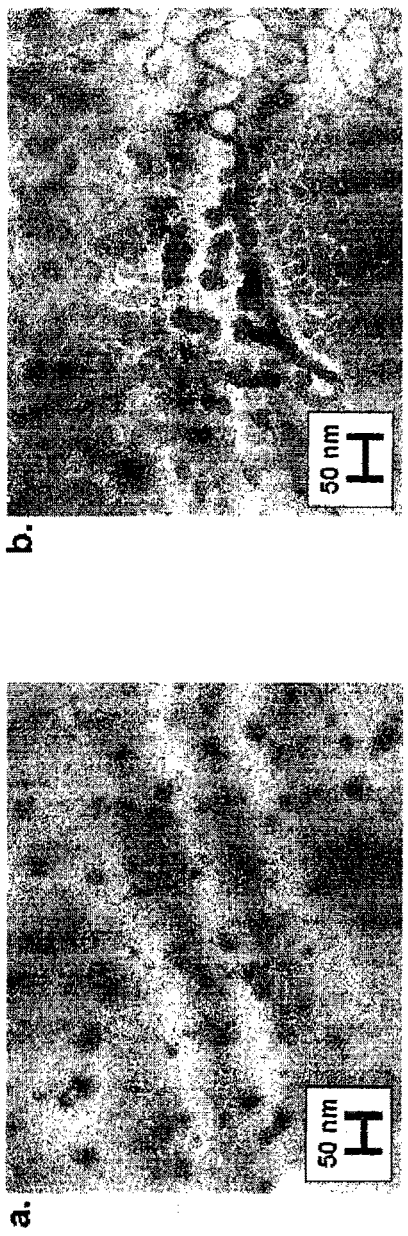
Figure 3:
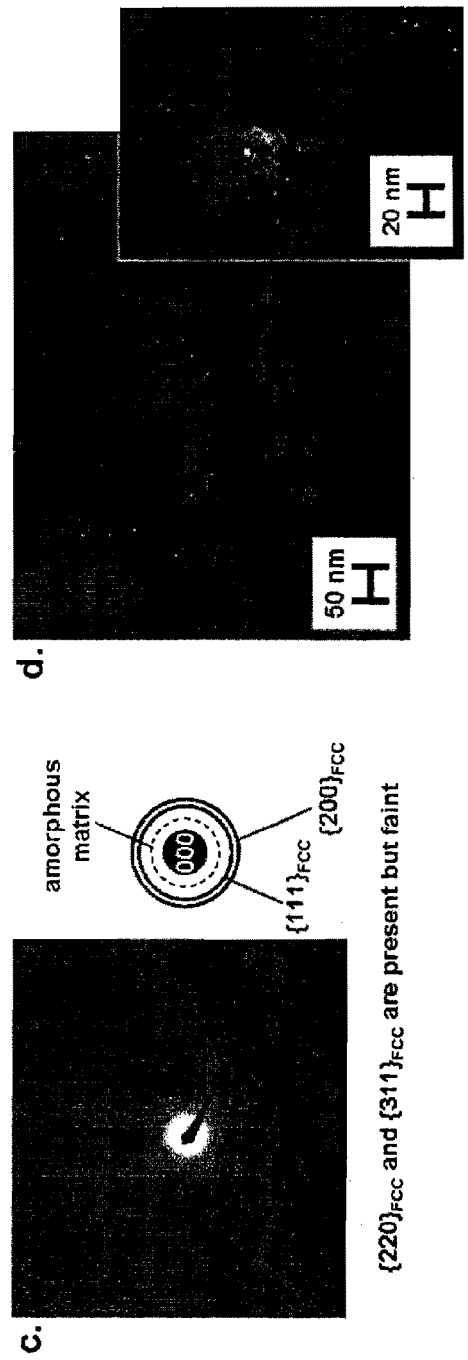
Figure 3:
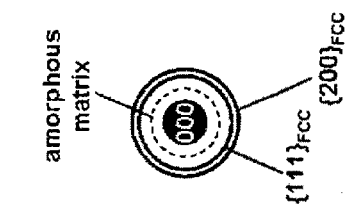

FIG. 3 shows characterization of Cu nanoparticles using TEM, with a-Fe particles shown for comparison. A BF image showing clusters of crystalline, metallic Cu nanoparticles is shown in FIG. 3A. A BF image of the amorphous matrix is shown in FIG. 3B. A SAD pattern identifying the nanoparticles in FIG. 3A as an FCC phase with a lattice parameter of approximately 360 pm and a random crystallographic orientation is shown in FIG. 3C. Centered DF image prepared using a portion of the {111} FCC ring is shown in FIG. 3D. The nanoparticles appear bright, on a dark background, indicating that the {111} FCC diffraction maxima originated from the nanoparticles and not the matrix (since the Cu particles are randomly oriented, many of the particles are out of contrast). The inset shows clumped and individual a-Fe particles (DF from a portion of the {110} BCC ring). Scale bars shown in FIGS. A, B, and D represent 50 nm. Scale bars in the insert represent 20 nm.

Figure 4:
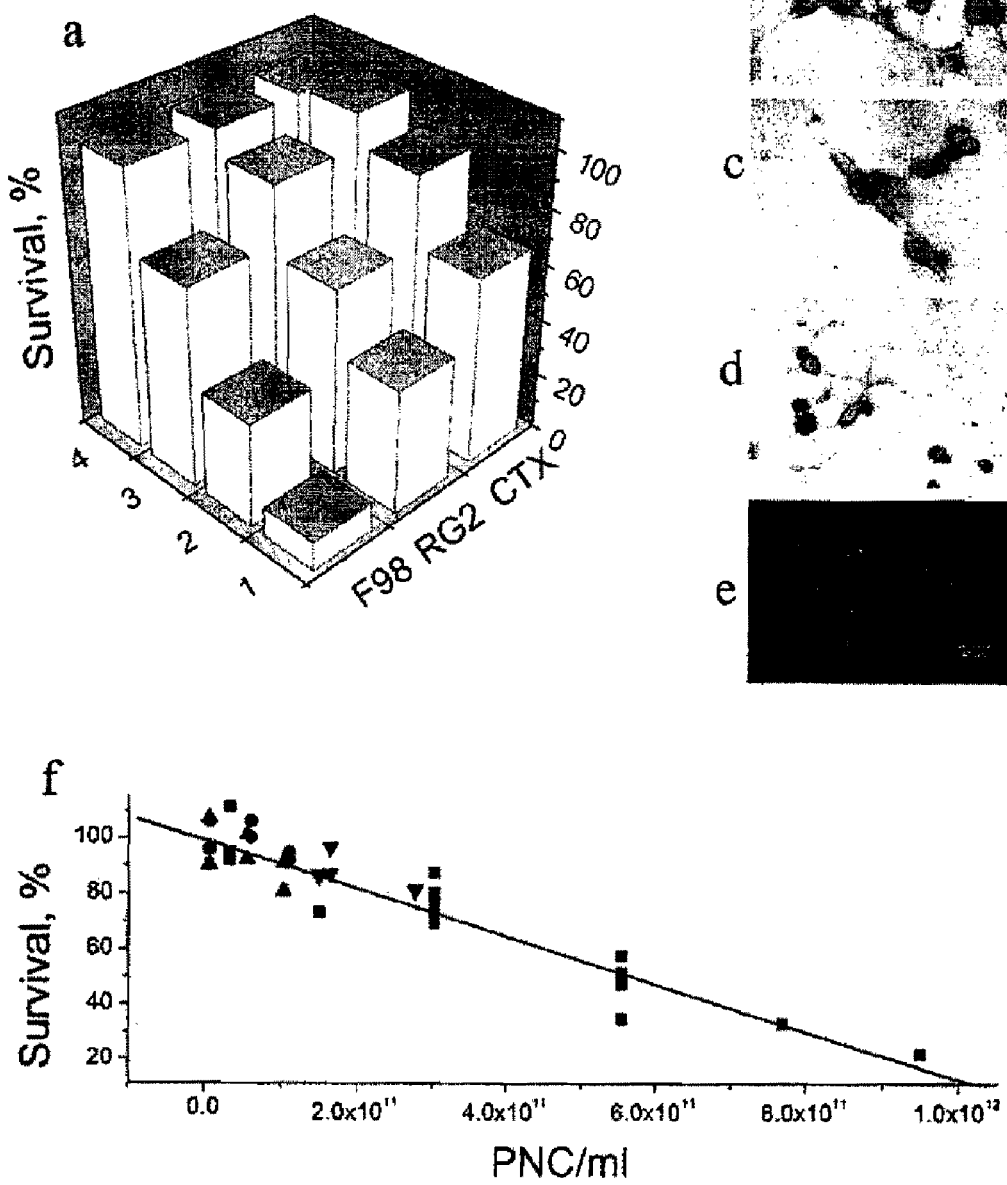

FIG. 4 shows the effect of PNC on cell viability. FIG. 4A shows the viability of cultured cells after 20 hours of exposure to PNC obtained from the shark blood at different concentrations of PNC/ml: (1)—$1.7 \times 10^{11}$; (2)—$9.1 \times 10^{10}$; (3)—$9.9 \times 10^9$; (4)—0. (F98, RG2—rat and mouse brain glioma cells, respectively, CTX—rat transfected astrocytes). FIGS. 4B-4E show dark-field photomicrographs of the mouse rat glioma cells. FIGS. 4B and 4C show cells before and after exposure to $7.7 \times 10^{11}$ PNC/ml, respectively. FIG. 4D shows cells after exposure to 1.0 μM staurosporine. 4-Fluorescence photomicrograph of RG2 glioma cell exposed to $7.7 \times 10^{11}$ PNC/ml for 20 h and stained with Annexin V and propidium iodide (400×). FIG. 4E shows viability of RG2 glioma cultured cells after 20 hours of exposure to PNC obtained from the blue shark (Prionace) (■), hound dog, (●), human (▲, and New Zealand white rabbit (Harland Sprague Dawley) (▼) blood at different concentrations. R=0.95, p<0.0001.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Compositions and methods for identifying and characterizing disease states are provided. The compositions comprise misfolded proteins and misfolded proteins aggregated on a nucleation center. The aggregated proteins are referred to herein as proteons. The nucleation centers are referred to as proteon nucleation centers (PNCs).

Definitions

By "proteons" are intended protein bodies, generally on the order of a few tens of nanometers up to several microns across, comprised of misfolded or partially misfolded proteins surrounding a PNC. Thus, the diameter of the proteon can be (but is not limited to) sizes of at least 10 nm, 20 nm, 30 nm, 40 nm, 50 nm, 60 nm, 70 nm, 80 nm, 90 nm, 0.1 μm, 0.2 μm, 0.25 μm, 0.3 μm, 0.4 μm, 0.5 μm, 0.61 μm, 0.71 μm, 0.8 μm, 0.9 μm, 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, or larger. In one aspect of the invention, proteons can be isolated from blood, including human, bovine, horse, pig, cat, dog, fish (including but not limited to teleosts such as sharks), rabbit, and rat blood. In another aspect of the invention, proteons can be isolated from plasma, including human, bovine, horse, pig, cat, dog, fish (including but not limited to teleosts such as sharks), rabbit and rat plasma.

By "PNC" is intended the metallic nucleation centers isolated as described herein. In one aspect of the invention, PNCs can be isolated from the blood, including human, bovine, horse, pig, cat, dog, fish (including but not limited to teleosts such as sharks), rabbit, and rat blood. In another aspect of the invention, PNCs can be isolated from plasma, including human, bovine, horse, pig, cat, dog, fish (including but not limited to teleosts such as sharks), rabbit, and rat plasma. PNCs may be comprised of, but not limited to, at least 1 nm, at least 2 nm, at least 3 nm, at least 4 nm, at least 5 nm, at least 10 nm or larger metallic clusters containing at least 10, 20, 30, 40, 50, 60, 70, 80, 90, 100, 200, 300, 400, 500, 600, 700, 800, 900, 1000, or more metal or metalloid atoms.

By metal (or metallic) cluster (also termed nanocluster) it is intended an aggregate of bonded metal atoms wherein valence electrons are delocalized and/or shared among constituent atoms, including but not limited to metals such as Cu, Zn, Fe, Mn, Cr, Mo, Mg, Sn, V, Ni and the like, as well as metalloids such as Se, Si, As, B, and the like, for example. Atoms that comprise such particles may be found in combination with other metals, such as for example in alloys. Atoms comprising the cluster may be in any reduction state.

By "plasma" is intended the supernatant produced by the centrifugation of blood or other suspension of biological material, including but not limited to dilutions of such supernatants with diluents.

By "seeding" is intended adding an amount of either a PNC or proteon to a biological sample.

The proteons of the invention can be identified and quantified in biological samples. Such samples include serum, blood, other bodily fluids, tissue including brain, other organ tissue, and the like. To identify the proteons in tissue, the tissue is homogenized in a fluid or liquid.

Proteons can be isolated from biological samples of any mammal including but not limited to human, primate, bovine, cattle, horse, sheep, pig, cat, dog, rabbit, rat, deer, ox, mouse, and the like. They can also be detected in samples from fish (including but not limited to teleosts such as sharks), chicken, turkey, duck, and the like.

As indicated, proteons are comprised of misfolded proteins. In one aspect, the proteon compositions of the invention show an apple-green birefringence when stained with congo-red. This staining pattern is analogous to that obtained with prions and other amyloid proteins, all of which are included in the class of congophilic proteins. See Kelly (1996) *Curr. Opin. Struct. Biol.* 6:11-17. These proteins are associated with various disorders or disease states. Thus, the identification of proteons comprised of such proteins is indicative of a disorder or disease state. Likewise, the number of proteons in a sample comprised of such proteins is predictive of the progression of the disease. That is, the number of proteons in a sample correlates with progression of a disease state. Therefore, quantification of proteons in a sample is useful for determining or diagnosing the stage of disease or disorder and can help in planning treatments or therapies for the disease. Examples of disorders involving misfolded proteins and the relevant proteins that can be utilized in the methods of the present invention are set forth in Table 1, below. The disorders associated with congophilic proteins are set forth in Table 2, below.

It is recognized that for proper diagnosis, proteons must not only be identified, but also the misfolded protein in the proteon must be identified. Methods for protein purification and identification include antibody binding, amino acid sequencing, and the like.

TABLE 1

Conformational diseases.
See Carrel and Lomas (1997) Lancet 350: 134-138; Carrell and Gooptu (1998) Curr. Op. Struc. Biol. 8: 799-809.; Soto (2001) FEBS Letters 498: 204-207; Jaikaran and Clark (2001); Ursini et al. (2002) Trends Mol. Med. 8: 370-374; Kannan et al. (1988) J. Biol. Chem. 263: 13766-13773; Schluter and Drenckhahn (1986) PNAS 83: 6137-6141; Gerner et al. (2002); Davis et al. (2002) Lancet 359: 2242-2247; Fernandez et al. (2001) Atherosclerosis 158, 103-111(atherosclerosis); Papalexis et al. (2001) Mol. Biochem. Parasitology 115: 77-86; Esievo et al. (1984) Veterinary Parasitology 15: 181-185; Igoe et al. (2002) Clin. Microb. Newsletter 24: 69-70; Kreidl et al. (2002) J. Am. Coll. Surgeons 194: 387; Beckers (2001) Netherlands J.. Med 58: 204-207 (autoimmune diseases); Ismeno et al. (1999) Int'l J. Cardiology 69: 179-183; Klibansky et al. (1966) Toxicon 3: 213-216; Seibert et al. (2003) Toxicon 41: 831-839; Szabo et al. (2002) Thrombosis Research 107: 357-363; Kaioumova et al. (2001) Chemosphere 43: 801-805.

| Protein | Disease |
|---|---|
| Hemoglobin | Sickle cell anemia and aggregates |
| | Heinz bodies in aged erythrocytes |
| | Unstable hemoglobin inclusion body hemolysis |
| | Drug induced inclusion body hemolysis |
| | Aggregates regulate apoptosis in cancer patients |
| | Atherosclerosis |
| | Malaria |
| | Infections |
| | Auto-immune disorders |
| | Toxic reactions |
| | Internal bleedings |
| Prion protein | Creutzfeld-Jacob disease (CJD) |
| | New variant CJD |
| | Bovine spongiform encephalopathy (BSE) |
| | Gerstmann-Straussler-Schheinker disease |
| | Fatal familial insomnia |
| | Kuru |
| β-amyloid | Alzheimer's disease |
| | Down's syndrome |
| | Familial Alzheimer's |
| α-Synuclein | Parkinson's disease, Lewy bodies |
| Tau protein | Frontotemporal dementia, Pick bodies |
| Serpins | $\alpha_1$-antitrypsin deficiency |
| | cirrhosis |
| | emphysema |
| | Antithrombin deficiency |
| | thrombosis |
| | $C_1$-inhibitor deficiency |
| | angioedema |
| Neuroserpin | Neurodegenerative disease, Collins bodies |
| Glutamate repeats | Inherited neurodenegerative disorders |
| | Hungtington's disease |
| Amylin | Diabetes type II |
| SOD | Amyotrophic lateral sclerosis |
| ApoB | Atherosclerosis |
| CFTR protein | Cystic fibrosis |
| Immunoglobulin | Systemic amyloid light chain amyloidosis |
| Amyloid light chain | Nodular amyloidosis |
| Serum amyloid A | Reactive systemic amyloid A amyloidoses |
| | Chronic inflammatory disease |
| Transthyretin | Senile systemic amyloidosis |
| | Familial amyloid neuropathy |
| | Familial cardiac amyloid |
| $\beta_2$-microglobulin | Hemodialysis amyloidosis |
| | Prostatic amyloid |
| Apolipoprotein AI | Familial amyloid polyneuropathy |
| | Familial visceral amyloid |
| Cystatin C | Hereditary (Icelandic) cerebral angiopathy |
| Lysozyme | Familial visceral amyloidosis |

TABLE 2

Congophilic disorders.
See Kelly (1996) Curr. Opin. Struct. Biol. 6: 11-17.

| Disorder Acronym | Disorder | Protein Involved |
|---|---|---|
| CJD | Spongiform encepalopathies | Prion protein fragments |
| APP | Alzheimer | Beta protein fragment 1-40/43 |
| HRA | Hemodialysis-Related Amyloidosis | Beta-2 microglobin* |
| PSA | Primary Systematic Amyloidosis | Immunoglobulin light chain and fragments |
| SAA 1 | Secondary Systematic Amyloidosis | Serum amyloid A 78 residue fragment |
| FAP I** | Familial Amyloid Polyneuropathy I | Transthyretin fragments, 50+ alleles |
| FAP III | Familial Amyloid Polyneuropathy III | Apolipoprotein A-1 fragments |
| CAA | Cerebral Amyloid Angiopathy | Cystatin A minus 10 residues |
| FHSA | Finnish Hereditary Systemic Amyloidosis | Gelsolin 71 residue |
| IAPP | Type II Diabetes | Islet amyloid polypeptide fragment |
| ILA | Injection-Localized Amyloidosis | Insulin |
| CAL | Medullary Thyroid Carcinoma | Calcitonin fragments |
| ANF | Atrial Amyloidosis | Atrial natriuretic factor |
| NNSA | Non-Neuropathic Systemic Amylodosis | Lysozyme and fragments |
| HRA | Hereditary Renal Amyloidosis | Fibrinogen fragments |

*Homologous to immunoglobin, thus a predicted paralogous disease.
**Also called senile systemic amyloidosis, prealbumin is synonymous with transthyretin. See mad-cow.org/congo.html. (the prefix "www" is required).

Immunohistochemical assays have been developed for the proteins listed in Tables 1 and 2. See, e.g., Hardt et al. (2000) J. Comp. Path. 122:43-53 (antibodies for the detection of the prion protein, PrP). However, many of these proteins are only abundant in the late stages of the disease and may be undetectable utilizing standard assay techniques. Thus, in one embodiment, the methods of the present invention may be combined with an immunochemical assay for the protein or proteins selected from Tables 1 and 2. These proteins, or their functional derivatives, may be detectably labeled with any appropriate marker such as a radioisotope, an enzyme, a fluorescent label, a paramagnetic label, or a free radical linked to an antibody capable of binding these proteins.

Methods of making and detecting such detectably labeled antibodies or their functional derivatives are well known to those of ordinary skill in the art, and are described in more detail below. See, for example, Klein (1982) *Immunology: The Science of Self-Nonself Discrimination* (John Wiley & Sons, New York 1982); Kennett et al. (1980) *Monoclonal Antibodies and Hybridomas. A New Dimension in Biological Analyses*, (Plenum Press, New York; Campbell (1984) *Monoclonal Antibody Technology, Laboratory Techniques in Biochemistry and Molecular Biology*, Volume 13, ed. Burdon et al. (Elsevier, Amsterdam; and Eisen (1980) in *Microbiology*, ed. Davis et al. 3d ed.; Harper & Row, Philadelphia. Methods for the generation of polyclonal antibodies are known, as are techniques for the generation of monoclonal antibodies See, e.g., Kohler and Milstein (1975) *Nature* 256:495-497.

Assay techniques useful in the present invention include, but are not limited to, assays comprising incubating a biological sample from a subject suspected of having such a condition in the presence of a detectably labeled binding molecule (e.g., antibody) capable of identifying the relevant protein, and detecting the binding molecule which is bound in a sample. See, e.g., Work et al. (1978) *Laboratory Techniques and Biochemistry in Molecular Biology* (North Holland Publishing Company, NY).

Alternatively, the proteins contained in a particular sample of proteons can be identified by screening against a panel of phage antibodies in which the displayed peptide is a domain of the antibody molecule that includes the site that binds antigen. Phage-antibody libraries can be constructed including billions of clones, displaying billions of antibodies with different antigen specificities. For a review of this technique, see Petrenko and Vodyanoy (2003) *J. Micro. Meth.* 53:253-262.

The presence of proteons themselves can be detected and quantitated by dark-field microscopy. Under high-resolution dark-field microscopy proteons are visualized as bright spherical shapes. Techniques for dark-field microscopy are known in the art. See, e.g., Bradbury and Bracegirdle (1998), *Introduction to Light Microscopy* (Microscopy Handbooks, No 42), 2d ed.; (Springer Verlag). In particular, proteons are small, ball-like bodies of different sizes, estimated in the range of 50-250 nm. By contrast, healthy erythrocytes appear as bright void circles of about 7 microns diameter in the dark-field view, whereas neutrophils are roughly 7-15 microns. When a blood sample becomes aged, the morphology and number of the proteons change, with some estimated to be 500 nm in diameter. Some appear attached to the internal surface of the erythrocyte membrane. Proteons are found in fresh blood of species including human, bovine, horse, pig, cat, dog, fish (including but not limited to teleosts such as sharks), rabbit, and rat blood.

Dark-field microscopy of proteons can be confirmed by transmission electron microscopy (TEM) and scanning electron microscopy (SEM) methodology. Techniques for electron microscopy are known in the art. See, e.g., Slayter and Slayter (1992) *Light and Electron Microscopy*, (Cambridge University Press).

Proteons can be isolated from blood or plasma, i.e., the supernatant produced by centrifuging a biological material. Centrifugal separation may be carried out by any means known in the art using any method, apparatus, time, temperature, or speed as appropriate for the biological sample. The relative centrifugal force (R.C.F) applied can be at least 300×g, 500×g, 600×g, 700×g, 800×g, 900×g, 1,000×g, 1,100×g, 1,200×g, 1,300×g, 1,400×g, 1,500×g, 1,600×g, 1,700×g, 1,800×g, 1,900×g, 2,000×g, 2,500×g, 3,000×g, 4,000×g, 4,500×g, 5,000×g, 5,500×g, 6,000×g, 6,500×g, 7,000×g, 7,500×g, 8,000×g, 8,500×g, 9,000×g, 9,500×g, 10,000×g, 11,000×g, 12,000×g, 12,800×g, 13,000×g, 14,000×g, 15,000×g, 16,000×g, 17,000×g, 18,000×g, 19,000 20,000×g, or more. The relative centrifugal force is a function of the rotor diameter and the revolutions per minute and is readily calculated from formula $R.C.F.=1.118\times10^{-5}\times r\times N^2$ (where r=the rotating radius and N=revolutions per minute). The time of centrifugation to obtain separation can be adjusted based on the R.C.F. applied and, thus, may be at least 10 sec, 20 sec, 30 sec, 40 sec, 50 sec, 1 min, 5 min, 10 min, 15 min, 20 min, 30 min, 40 min, 50 min, 1 h, 1.5 h, 2 h, 2.5 h, 3 h, 4 h, 5 h, 6 h, 8 h, 10 h, 12 h, 14 h, 16 h, 18 h, 24 h, or more. The temperature of the sample may be maintained within a suitable range before during, and/or after separation, such as for example at least 4° C., 14° C., 25° C., 37° C., 40° C., 42° C., 56° C., 65° C., 90° C., or more.

In one embodiment, proteons can be formed by incubating plasma at 37° C. under sterile conditions over a thirteen day period. At the end of this period, the numbers of proteons observed under dark-field light microscopy are greatly increased.

In another embodiment, large numbers of proteons are produced by subjecting plasma to 120° C. at 20 psi for two hours. The visible number of proteons is amplified by subjecting plasma to a single step of elevated temperature.

Efficiency of proteon production is enhanced by taking a small portion of an amplified sample, adding it to an untreated sample, and heating the untreated sample. These steps can be repeated a number of times, each iteration yielding an increased quantity of proteons. Accordingly, by dividing the sample into a number of subsamples, subjecting the first subsample to heat or pressure, then aliquoting a small amount of the proteons from the first subsample into the second subsample and carrying out the heating step, a greater concentration of proteons can be produced from the second subsample than was produced from the first subsample. These seeding steps can be repeated multiple times until, after several iterations, the concentration of proteons produced per volume of sample eventually plateaus.

Typically, the first two cycles result in a small but significant increase of proteon population, whereas the third cycle brings about a dramatic increase in the number of proteons. Generally, the next three cycles result in saturation of the proteon population.

In one embodiment, a test sample containing a small amount of misfolded proteins is subjected to a single heating step. The amplified proteons are quantitated by dark-field microscopy and verified by immunofluorescent techniques to detect the misfolded protein.

In another embodiment, a small amount of seeds such as the PNCs described above can be added to a test sample to increase the sensitivity of the single step methods. Roughly $5\times10^{13}$ PNC/ml are produced by initial filtration of plasma through at least a 5 kDa nominal molecular weight (NMW) cutoff filter, at least a 4 kDa NMW cutoff filter, at least a 3 kDa NMW cutoff filter, at least a 2 kDa NMW cutoff filter, at least a 1 kDa NMW cutoff filter, at least a 500 Da NMW cutoff filter, or smaller, or a combination thereof. The sample may be optionally prefiltered using a 0.5 micron filter, a 0.22 micron filter, a 0.2 micron filter, at least a 100 kDa NMW cutoff filter, a 50 kDa NMW cutoff filter, a 30 kDa NMW cutoff filter, any filter within the range of 5 kDa to 10, 20, 30, or higher molecular weight cutoff, or any combination thereof. This concentration then can be increased by a factor of roughly 100 by evaporation. Thus, in one aspect, addition of 5 ml of $5\times10^{13}$ PNC/ml to a 1 ml sample increases the concentration of PNC in a sample by $2.5\times10^{11}$ PNC/ml. This concentration is increased by a factor of 100 if pre-concentrated PNC are added. If the initial concentration of PNC varies from $10^8$ to $10^{11}$ PNC/ml, the sensitivity can be increased by a factor of between 250 to 250,000.

In another embodiment, the first step amplification described above is carried out, then a small portion of amplified sample is introduced into the untreated sample and subjected to heat again. Then, the small portion of the second amplified sample is added to the third untreated sample, heated, and so on. The number of cycles depends on the initial concentration of misfolded proteins. Suitable numbers of cycles include 1, 2, 3, 4, 5, 6, 7, 8, 9, 10, 15, 20, 25, or more.

In one embodiment, the detection and identification can be done as a single-step method. Apparatus for subjecting a sample to heat and/or pressure are recognized in the art and include without limitation, PCR thermocyclers, autoclaves, etc.

As will be recognized by one of skill in the art, both the single- and multiple-step methods can be manipulated by varying the temperature, pressure, or temporal parameters. Suitable temperatures include at least 4, 15, 25, 37, 40, 45, 50, 55, 56, 60, 65, 70, 75, 80, 85, 90, 95, 100, 105, 110, 115, 120° C., or higher. Suitable pressures include at least ambient pressure, as well as at least 14, 15, 16, 17, 18, 19, 20, 21, 22, 23, 24, 25 psi, or higher. Suitable times of treatment include at least 1, 5, 10, 15, 20, 25, 30, 25, 40, 45, 50, 55, 60, 65, 70, 75, 80, 85, 90, 95, 100, 105, 110, 115, 120 minutes, or more and may include times of treatment of at least, 4, 5, 6, 7, 8, 9, 10, 11, 12, 13, 14, or more days.

In another embodiment, these methods can be utilized to clear misfolded proteins from a biological sample such as blood. Because low temperatures can be utilized with long time periods, this can be accomplished without damaging the biological sample.

In another embodiment, these methods can detect misfolded proteins involved in congophilic disorders. See Kelly (1996) Curr. Op. Struc. Biol. 6:11-17; Kelly (1996) 8:101-106. For instance, there is a demonstrated structural homology between prion and hemoglobin proteins. Korth et al. (1997) Nature 390:74-77. There is evidence that prions are present in lymphoid organs and blood. See, e.g., Brown et al. (2001) J. Lab. Clin. Med. 137:5-13; Aguzzi (2000) Lab. Clin. Med. 137:5-13; Aguzzi (2001) Nature Medicine 7:289-290; Wadsworth et al. (2001) Lancet 358:171-180. Accordingly, the methods of the present invention can be utilized for amplification of a congophilic protein, thus allowing early detection of disorders related to these proteins.

PNC of roughly 1-2 nm and containing about 40-300 atoms play an important role in capturing hemoglobin released into blood plasma. While released hemoglobin is normally captured by protein haptoglobin and endocytosed by macrophages, released hemoglobin can be collected by PNCs. Roughly $7 \times 10^{13}$ PNC are present in each milliliter of human blood, while only 0.003% of the whole pool of PNC is normally linked to proteins and made into proteons. However, a proteon of medium size of 160 nm can collect about 100,000 protein molecules of similar size to hemoglobin. Thus, the strong protein scavenging properties of metal nanoparticles allow them to collect proteins including misfolded hemoglobin (Kristiansen et al. (2001) Nature 409:198).

Thus, in another embodiment, the present methods can be utilized for amplification of proteins involved in intravascular hemolysis and resulting in aggregation of hemoglobin, including, without limitation, sickle cell anemia, atherosclerosis, malaria, infections and their complications, auto-immune disorders, internal bleedings and intravascular hemolysis due to internal prosthetic devices, and toxic reactions. See Kannan et al. (1988) J. Biol. Chem. 263:13766-13773; Schluter and Drenckhahn (1986) PNAS 83:6137-6141 (sickle cell); Fernandez et al. (2001) Atherosclerosis 158, 103-111 (atherosclerosis); Papalexis et al. (2001) Mol. Biochem. Parasitology 115:77-86; Esievo et al. (1984) Veterinary Parasitology 15:181-185; Igoe et al. (2002) Clin. Microb. Newsletter 24:69-70; Kreidl et al. (2002) J. Am. Coll. Surgeons 194:387; Beckers (2001) Netherlands J. Med:58:204-207 (autoimmune diseases); Ismeno et al. (1999) Int'l J. Cardiology 69:179-183; Klibansky et al. (1966) Toxicon 3:213-216; Seibert et al. (2003) Toxicon 41:831-839; Szabo et al. (2002) Thrombosis Research 107:357-363; Kaioumova et al. (2001) Chemosphere 43:801-805.

Using standard techniques, samples for single-step or cyclic amplification can be prepared from homogenates of small tissue fragments, or from biological fluids such as blood, cerebrospinal, lymph, etc. Techniques for the preparation of tissue homogenates and biological fluids from such sources are known. See Sambrook et al. (1989) Molecular Cloning—A Laboratory Manual, Vols. 1-3 (2d ed; Cold Spring Harbour Laboratory Press, Plainview, N.Y.); and Ausubel et al., eds. (1994) Current Protocols in Molecular Biology, (Greene Publishing Associates, Inc. and John Wiley & Sons, Inc.).

PNCs can be produced from plasma by filtration through an ultrafiltration membrane. In one embodiment, plasma is filtered consecutively through a 30 kDa and a 5 kDa Centricon™ filter from Millipore before heat treatment. The centrifuge filtration is carried out using an initial volume of 80 ml centrifuged at 3,500 g for 20 minutes, 20° C.

Filtration of plasma before heat treatment abolishes proteon formation in the retentate. However, recombination of the fractions results in the resumption of proteon formation, and the number of proteons formed is dependent upon the amount of filtrate added back to the retentate. Thus, the PNCs are present in the filtrate.

Adsorption spectra of the filtrate reveals the presence of metals, including copper, zinc, and iron, indicating that PNCs comprise metals. The filtrate was precipitated with 1.2 mM $MgSO_4$ and TEM studies were carried out. Such procedures are known in the art. See, e.g., Shindo and Oikawa, Analytical Electron Microscopy for Materials Science, Springer-Verlag (2002). It was found that the precipitated extract contained crystalline metallic nanoparticles of roughly 1-2 nm diameter. Selected area diffraction patterns were consistent with the presence of face centered cubic (FCC) or body centered cubic (BCC) metals or solid-solution alloys such as FCC copper and BCC iron.

For a review of metal clusters, see Aiken and Finke (1998) J. Mol. Cat. A:Chem. 145:1-44; Gonzalez-Moraga (1993) Cluster Chemistry (Springer-Verlag, New York, N.Y.). High symmetry is one of the main characteristics of metal clusters (Gonzalez-Moraga (1993) (Supra). In addition, metal clusters bind proteins. See Broun et al. (2002) J. Mol. Biol. 321:341-353; Liu and Xu (2002) J. Inorganic Biochem. 88:77-86. Thus, in one embodiment, the PNCs of the invention are characterized by small size, a few nm or smaller. Additionally, the PNCs are present in large quantities, about $10^{12}$-$10^{13}$ PNC/$cm^3$ of blood or tissue, are abundant, present binding sites and strong affinity to proteins, exhibit variability to bind different proteins, and resist extreme physical and biochemical conditions.

To test the effects of PNCs isolated from the filtrate upon living cells, various amounts of PNCs obtained by ultrafiltration and sterilized by autoclaving were incubated for four hours with various animal cells in tissue culture. Significant effects upon cell viability were observed, such as apoptosis of cells and cell death. For instance, rat and mouse glioma cells demonstrated marked signs of cell death, as assessed both microscopically and by MTT assay. Accordingly, the PNCs of the invention comprise a novel reagent for use in inducing apoptosis, as well as a process for its production. In one embodiment, aliquots from 1 to 40 µl containing about $1 \times 10^{12}$ to $4 \times 10^{13}$ PNCs were added to 100 µl wells of 96-well ELISA plate. Such compounds and processes are of great usefulness to those of skill in the art. See, e.g., U.S. Pat. Nos. 5,344,926 to Murakata et al., titled "Process for producing staurosporine derivatives"; 4,973,552 to Schroeder et al., titled "Staurosporine fermentation process"; and 6,518,032 to Fritz et al., titled "Rapid methods for identifying modifiers of cellular apoptosis activity."

Various concentrations of PNCs and or proteons can be used to mediate biological effects. For example, concentrations of at least $5 \times 10^{11}$, $1 \times 10^{11}$, $5 \times 10^{10}$; $1 \times 10^{10}$, $5 \times 10^9$; $1 \times 10^9$, $5 \times 10^8$; $1 \times 10^8$, $5 \times 10^7$; $1 \times 10^7$, $5 \times 10^6$; $1 \times 10^6$, $5 \times 10^5$; $1 \times 10^5$, $5 \times 10^4$; $1 \times 10^4$ or less may be used.

This invention is further illustrated by the following examples that should not be construed as limiting.

EXPERIMENTAL

Example 1

Production of Proteons from Blood and Analysis by Microscopy

A 30 μl sample of freshly drawn full blood from a healthy human male was obtained and diluted in 1000 μl of purified water (produced from Millipore's DIRECT Q™ water purification unit with 17 MOhm resistivity) in a 1.5-ml plastic vial, and centrifuged at 2200×g (6000 rpm) to obtain plasma. An additional aliquot of the blood was taken and prepared for optical dark-field microscopy. The plasma was transferred to a 4-ml glass vial with a plastic cap and a teflon liner. An aliquot of plasma was again retained for dark-field microscopy. The vial and contents were subjected to heating at a temperature of 120° C. and 20 psi of pressure for two hours. An aliquot of the heat-treated plasma was prepared for dark-field microscopy.

Each aliquot retained for microscopy was analyzed by dark-field microscopy using an Olympus™ microscope fitted with a 100 W mercury lamp, a polarizer, and a Naessens dark-field condenser (COSE Corp., Canada).

After analysis, the fresh full blood sample was found to contain approximately $3 \times 10^8$ proteons/ml, whereas the diluted sample contained roughly $9 \times 10^6$ proteons/ml. The treated sample contained an estimated $3 \times 10^{11}$ proteons/ml, a five-order of magnitude increase. Adjusted for the initial dilution of the blood sample, each milliliter of blood yielded roughly $1 \times 10^{13}$ proteons. Thus, within two hours, the number of proteons increased by approximately 5 orders of magnitude. Assuming exponential growth, then the number of proteons (N) at any given moment of time (t) can be described by the equation:

$$N = N_0 e^{bt} \tag{1}$$

where $N_0$ is the initial number of particles, and b is the growth coefficient. If N, $N_0$, and t are substituted with the experimental values found in the above experiment, one can estimate that the growth coefficient (b) for this case is equal to 5.2 l/hour, and the proteon population is doubled every 8 minutes. A summary of the data is presented in

TABLE 3

Cyclic amplification methods[a].

| Temperature, ° C. | Time, regime | [b]Number of proteons in 1 ml | [c]Media | Number of experiments |
|---|---|---|---|---|
| 37 | [d]1 cycle, 12 days | $7.0 \times 10^{10}$ | Plasma | 8 |
| 37 | [d]1 cycle, 12 days | $3.5 \times 10^{11}$ | Growth media 1 | 8 |
| 37 | [d]1 cycle, 12 days | $3.0 \times 10^{11}$ | Growth media 2 | 8 |
| 40 | 1 cycle, 90 min | $3.6 \times 10^8$ | Plasma | 8 |
| 40 | 6 cycles/15 min | $1.4 \times 10^8$ | Plasma | 8 |
| 56 | 1 cycle/15 min | $1.8 \times 10^9$ | Plasma | 8 |
| 56 | 6 cycles/15 min | $2.0 \times 10^9$ | Plasma | 8 |
| 65 | 3 cycles/15 min | $2.5 \times 10^{11}$ | Plasma | 15 |
| 65 | 6 cycles/15 min | $2.5 \times 10^{11}$ | Plasma | 15 |
| 90 | 1 cycle/3 min | $5 \times 10^{11}$ | Plasma | 9 |
| 120° C., 140 kPa | 1 cycle/<1 min | $8 \times 10^{11}$ | Plasma | 12 |
| 120° C., 140 kPa | 1 cycle/2 hours | $8 \times 10^{11}$ | Plasma | 245 |

[a]The first sample was incubated for 15 minutes at temperatures shown herein. Five microliters of the treated first sample are introduced as seeds in the untreated second one and subjected to the same heat again. Then, 5 microliters of the second amplified sample are added to the third untreated sample, heated and so on up to 6 cycles.
[b]Number of proteons was estimated by counting with high resolution dark-field microscope and electron microscopy.
[c]Media. Plasma was obtained from a blood as described herein. D5648, growth media 1, D5648 tissue culture media (Sigma) with 10% FBS (HyClone); D6429, growth media 2, D6429 tissue culture media (Sigma) with 10% FBS.
[d]Proliferation of proteons is characterized by a 5 day latent period, a 2 day exponential growth phase, and 5 days of saturation.

As a control, a suspension of phospholipids and cholesterol was subjected to the same protocol used for the blood sample. However, no structures resembling proteons were observed under dark-field microscopy.

Electron microscopy analysis was also carried out on samples obtained before and after heat treatment. Transmission electron microscope (TEM) images obtained from pre- and post-heat-treatment samples reveal small proteons appearing as dark discs with a rough and fibrous appearance. An analysis of the TEM images revealed the size distribution of this characteristic small proteon to reach a maximum about 150 nm.

Another characteristic form of proteon was observed, a coconut-shaped particle of about 1-5 microns with a structure resembling one or more nuclei and a cell-like appearance. The nuclei look very similar to the small proteons described above. A cross-sectional view of a larger proteon reveals a very distinctive external membrane-like structure. This membrane-like structure, however, looks very different from the bacterial wall or the mammalian cell membrane, appearing as a curly fibrous shell of 10-12 nm thick. Some fiber-like structures and a few nuclei are visible inside the proteon. Images obtained by scanning electron microscopy (SEM) confirm the presence of both small and large characteristic proteons.

Example 2

Chemical Composition of Proteons

Energy Dispersive Spectroscopy Analysis

The chemical composition was determined by energy dispersive X-ray spectroscopy using a JEOL JSM-840 SEM system using standard procedures for identifying and quantifying elemental composition. Such procedures are known in the art. See, e.g., Shindo and Oikawa (2002) Analytical Electron Microscopy for Materials Science (Springer-Verlag).

A sample of proteons suspended in distilled water was deposited on the aluminum SEM mount and dried in a vacuum for 24 hours. The X-ray spectra were obtained with an electron beam size of 200 nm at 80 kV for 90 s. Spectra revealed that the proteons were composed of carbon, oxygen, nitrogen, and sulfur, and the presence of potassium, sodium, chloride, silicon, and copper was also detected. The presence of carbon, nitrogen, and sulfur was confirmed by analytical chemical analysis (Leco Corporation, Michigan, USA). Notably phosphorus, a necessary element of DNA, was never detected in the proteon samples. On the other hand, all the elements needed for amino acids and proteins are available.

Amino Acid Composition

Free amino acid composition of samples before and after heat and high pressure treatment were determined (LPSA, University of Arizona, Tucson, Ariz.). See Table 4.

TABLE 4

| | Amino acid composition (pmol/50 ul) | | |
|---|---|---|---|
| No | Amino acid | Control* | Proteons |
| 1 | O-Phosphoserine | 98.731 | 39.878 |
| 2 | Taurine | 191.790 | 227.739 |
| 3 | O-Phosphoethanolamine | 17.980 | 15.318 |
| 4 | Urea | 220.811 | 62.573 |
| 5 | Aspartic Acid | 137.212 | 123.086 |
| 6 | Threonine | 365.225 | 214.981 |
| 7 | Serine | 385.160 | 314.039 |
| 8 | Asparagine | — | 95.908 |
| 9 | Glutamic Acid | 483.645 | 229.149 |
| 10 | Glutamine | 287.073 | 3.920 |
| 11 | Glycine | 985.419 | 922.430 |
| 12 | Alanine | 443.165 | 448.792 |
| 13 | Citralline | 81.803 | — |
| 14 | Valine | 188.720 | 236.126 |
| 15 | Cystine | 4.799 | 6.367 |
| 16 | Methionine | — | 77.583 |
| 17 | L-Cystathio-nine | 12.301 | 16.417 |
| 18 | Isoleucine | 82.836 | 76.302 |
| 19 | Leucine | 121.941 | 139.060 |
| 20 | Tyrosine | 68.636 | 75.682 |
| 21 | Phenylalanine | 104.921 | 79.904 |
| 22 | γ-Amino-butiric Acid | — | 108.022 |
| 23 | Etanolamine | 36.578 | 35.605 |
| 24 | L-Ornithine | 53.341 | 23.004 |
| 25 | Lysine | 226.033 | 208.597 |
| 26 | Histidine | 75.954 | 103.043 |
| 27 | Arginine | 273.221 | 166.512 |

*Pre-heat and high-pressure treatment plasma.

Protein Concentration

The quantitative analysis of proteins in the proteon samples was carried out by two different protein assays obtained from Bio-Rad Laboratories and Sigma according to the manufacturers' protocols. Samples of blood as described in the Example 1 were exposed to different temperatures and pressures. Results of the experiments are shown in

TABLE 5

| | Protein concentrations in proteon samples. | |
|---|---|---|
| Sample, Condition | BIO-RAD, Protein concentration, µg/ml | SIGMA, Protein concentration, µg/ml |
| Plasma, control, 25° C. | 0.67 ± 0.05 | 0.85 ± 0.2 |
| Plasma, 56° C., normal pressure, 10 min | 0.72 ± 0.04 | 0.98 ± 0.2 |
| Plasma, 80° C., normal pressure, 10 min | 0.68 ± 0.04 | 1.0 ± 0.2 |
| Proteons, 120° C., 20 psi, 2 hours | 0.71 ± 0.04 | 1.7 ± 0.2 |

Gel electrophoresis of plasma and two major protein components of plasma, albumin and hemoglobin, treated with 120° C. heat and 20 psi pressure produce obvious bands of 66,200 Da and 14,400 Da. These are shared with albumin and hemoglobin, respectively. After the treatment, the albumin has two weak bands of 14,400 Da and ~8,000 Da, which coincide with the same bands of proteons. The treated hemoglobin conserved only the 8,000 Da band. Proteons filtered through a 100 kDa filter conserved the 14,400 and ~8,000 bands, while proteons washed from the filter contain practically all bands of plain proteons, indicating that misfolded albumin and hemoglobin may be present in proteons. The confirmation of this fact may be obtained from the immunoblotting analysis.

Proteons from rabbit blood were disassembled by sodium dodecyl sulfate (SDS), a negatively charged detergent. The fragments of proteins were electrophoresed down and made distinctive bands in the polyacrylamide gel. The proteins were identified by N-terminal amino acid sequencing, yielding the partial sequence VLSPA(D/E)(E/K)TN(A/I) SEQ ID NO:1 that shows 100% homology with the rabbit alpha chain of hemoglobin. Amino acid analysis showed that proteons are enriched by hydrophilic negatively charged amino acids, glutamic and aspartic acids. Additionally, such proteons show a similar hydropathy index to hemoglobin. Proteons stained with congo-red show an apple-green birefringence with polarizing light indicating the anisotropic alignment of the dye molecules. Congo-red staining is indicative of a common structural feature shared by many amyloids. Specifically, they are stabilized in part by anti-parallel beta sheet extensions from one monomer to another. It is believed that the dye binds to inter-monomer clefts between anti-parallel beta edge strands. See Kelly (1996) Curr. Op. Struc. Biol. 6:11-17; Kelly (1996) Curr. Op. Struc. Biol. 8:101-106. One protein belonging to the congophilic family is the prion protein associated with the prion diseases. A structural homology between prion and hemoglobin proteins has been demonstrated (Korth et al. (1997) Nature 390:74-77). In particular, two prion PrP(121-231) molecules could be superimposed with two B subunits of the crystal lattice of sickle cell hemoglobin 1 HBS. The superposition included the backbone atoms of residues 145-154, 179-189, and 201-217 of the helices 1, 2, and 3 of PrP(121-231) and of residues 5-14, 106-116, and 125-141 of the helices 1, 6, and 7 of hemoglobin S.

Absence of DNA in Proteons

An aliquot of blood pre- and post-treatment (see Example 1) was purified using the DNeasy Tissue Kit™ (Qiagen) according to the manufacturer's standard protocols for animal blood and bacteria. After final elution, samples were loaded on 1% agarose gel. DNA bands were visualized with ethidium bromide. DNA was detected in pre-treatment sample and undetected in the post-treatment sample.

Similar results were obtained using a HIGH PURE™ PCR Template Preparation Kit from Roche for isolation of Nucleic Acids followed by fluorometric quantitation of double-stranded DNA using the PICOGREEN™ dsDNA Quantitation Reagent from Molecular Probes and a TECAN SPECTRAFLUOR PLUS™ equipped with DELTASOFT™ software for detecting fluorescence (excitation at 485 nm and emission at 535 nm). See Table 6.

TABLE 6

Fluorometric quantitation of DNA in blood and proteons.

| Sample | DNA concentration, µg/ml |
|---|---|
| Blood | 45.1 |
| Blood after dilution and centrifugation | 3.0 |
| Proteons, freshly prepared | 0.033 |
| Proteons, 3 months old | <0.001 |

Example 3

Controlled Growth of Proteons

Two identical sets of samples were prepared for this experiment, in which the growth of proteons incubated at 37° C. in an atmosphere of ambient air was compared with the growth of proteons incubated in an atmosphere of 5% $CO_2$. Each set included the following numbered groups:
  Group 1. Three ml of freshly prepared proteons (as described in Example 1).
  Group 2. Three ml of plasma after dilution and centrifugation (as described in Example 1).
  Group 3. Ten µl of freshly prepared proteons added to 3 ml of D6429 tissue culture media (Sigma) with 10% FBS (HyClone).
  Group 4. Ten µl of freshly prepared proteons added to 3 ml of D5648 tissue culture media (Sigma) with 10% FBS (HyClone).
  Group 5. Ten µl of freshly prepared plasma added to 3 ml of D6429 tissue culture media (Sigma) with 10% FBS (HyClone).
  Group 6. Ten µl of freshly prepared plasma added to 3 ml of D5648 tissue culture media (Sigma) with 10% FBS (HyClone).

The experiment was run in duplicate. Uninoculated media were used as a control. Samples were analyzed by dark-field and scanning electron microscopy at the time points of 0, 2, 4, 8, and 13 days.

Optical observation of proteons was performed with an OLYMPUS™ microscope fitted with a 100-W mercury lamp illumination source, a polarizer, a Naessens dark-field condenser (COSE Corp., Canada) and a 100× objective (oil, NA 1.4). The dark-field images were directed to a DEI-470T OPTRONICS™ CCD Video Camera System (Optronics Engineering, CA) utilizing the methods described in Vodyanoy et al. (1994) Langmuir 10: 1354-1357. A direct count of proteons was used to determine their concentrations in liquid samples, and IMAGE PRO™ (Creative Software, Inc.) was used to quantify the number of proteons.

The number of proteons incubated at 37° C. in an atmosphere of ambient air (Group 1) measured by dark-field microscope did not change significantly ($p<0.01$) during 13 days (FIG. 2A, line 1). The plasma at the same conditions (Group 2) showed a very small increase in population of proteons within 8 days of incubation, but the number increased dramatically and reached the number of proteons in group 1 after 13 days of incubation (FIG. 2A, line 2). Proteons and plasma in tissue culture media (Group 3 and 4, respectively) exhibited the same growth curves and reached the same number of proteons after 13 days of incubation (FIG. 2B). The culture media alone incubated at the same conditions showed no proteons (FIG. 2B, bottom line). No significant ($p<0.01$) effect of $CO_2$ was observed.

Example 4

Reversibility of Construction and Deconstruction of Proteons In Vitro

Plasma was prepared as described in Example 1. The samples of plasma were combined with the guanidine hydrochloride or urea to a final concentration of 0, 0.01, 0.1, 1, 4, and 8 M, respectively. These chaotropic compounds are known to unfold and denature proteins.

Samples were subjected to heat of 120° C. and pressure of 20 psi. In the samples to which no chaotropic compounds were added, the numbers of proteons observed by dark-field microscopy was normally high. The number of proteons decreased as the concentration of chaotropic compounds was increased (FIG. 2C).

Samples of proteons grown at the suppressive presence of 8 M Urea were subjected to dialysis using a Pierce SLIDE-A-LYSER™ 10K dialysis cassette (20 h, 5 L, 20° C.) according to the manufacturer's instructions. The number of proteons found by dark-field microscope increased significantly. Samples of plasma treated with 120° C. heat and 20 psi pressure and urea at concentrations of 0.01-8 M were taken. Polyacrylamide gel electrophoresis was carried out on each sample with a 4-20% Tris-HCl READY™ precast gel (Bio-Rad) according to the manufacturer's protocol. The control (proteons without chaotropic compounds) showed two characteristic bands of 14,400 and about 8,000 Da. The experimental samples (proteons in the presence of a chaotropic compound) displayed a diffuse distribution of proteins or fragments of proteins with no sharp bands of proteins of the high molecular mass range. As the concentration of urea increased, the intensity of the diffusion staining decreased, and almost fully disappeared at the 8 M concentration of urea. The proteon sample displays a 14,400 Da band that coincides with a similar band found in plasma. When guanidine hydrochloride or urea was added to proteons produced without the chaotropic compounds, heat of 120° C. and pressure of 20 psi resulted also in a great reduction of number of proteons visible by dark-field microscopy. Dialysis of these samples restored the population of the proteons. Gel electrophoresis of proteons and plasma treated with 120° C. heat and 20 psi pressure at the presence of urea, and then dialyzed, reveals two bands of 14,400 and about 8,000 Da in all samples, including those before and after dialysis.

Example 5

Effect of Ultrafiltration on Proteon Formation

PNCs were removed from blood plasma by filtering the plasma through 5 kDa CENTRICON™ filters from Millipore according to the manufacturer's protocol. The protein level in the retentate was quantitated and compared to that of unfiltered plasma. Assay kits were obtained from Bio-Rad Laboratories, and quantitative studies were carried out according to the manufacturer's instructions. The amount of protein in the filtered plasma was the same as that measured in the non-filtered sample. No protein was detected in the filtrate. After filtration, proteons could not be produced until the filtered fraction was returned to the plasma. The number of proteons was dependent on the amount of filtrate returned to the retentate. Addition of 10 mM of the chelating agent, ethylene diamine tetra acetate (EDTA), known to form strong complexes with metals, also prevented the formation of proteons. Adsorption spectra of the filtrate, determined by energy dispersive x-ray spectroscopy (EDS) and inductively coupled plasma—atomic emission spectrometry (GTW Analytical Services, TN), revealed the presence of metals, including Cu, Zn, and Fe.

Example 6

Analysis of PNCs

To characterize the nature of the PNC nanoparticles, transmission electron microscopy (TEM) was utilized. Transmission electron microscopy (TEM) was performed using a JEOL JEM™ 2010 instrument, operated at 200 kV. Bright-field (BF) imaging was used to provide an overview of the microstructure of the sample. Features of interest were characterized by selected area diffraction (SAD) and nanobeam diffraction (NBD), with the latter set up to produce a narrow (<50 nm diameter), yet near-parallel beam, so that SAD-like patterns were produced. Dark-field (DF) imaging was employed to determine which microstructural features gave rise to the diffraction maxima. The composition of microstructural features was determined (qualitatively) by means of energy dispersive x-ray spectroscopy (EDS). This work employed an Oxford Instruments' ultra-thin window (UTW) detector, attached to the JEM 2010™, together with an Oxford Instruments' ISIS™ analyzer.

Scanning electron micrographs were obtained using a JEPL JSM-840 SEM system. Plasma from rabbit blood was filtered consecutively through a 30 kDa and a 5 kDa CENTRICON™ filter from Millipore before heat treatment. PNCs were precipitated from the filtrate by 1.2 mM $MgSO_4$ at pH 11.3 and transferred onto 400 mesh Ni/carbon grids (Electron Microscopy Sciences). Proteon samples for TEM were fixed with 3% gluteraldehyde, dehydrated with ethanol, and embedded in Durcupan ASM™ resin (Fluka).

The bulk of the blood precipitate from rabbit plasma was amorphous. However, this extract was found to contain crystalline metallic nanoparticles, with diameters of around 1-2 nm and above. SAD patterns originating from different regions of the samples were consistent with the presence of both face centered cubic (FCC) and body centered cubic (BCC) metals (or possibly solid-solution alloys), with lattice parameters ($a_0$) of approximately 360 and 290 pm respectively. These combinations of Bravais lattice and $a_0$ are close to those of FCC copper ($a_0$=361.50 pm (International Centre Diffraction Data (2001), Powder Diffraction File, ICCD, Newtown Square, Pa.) and BCC α-iron ("ferrite", $a_0$=286.64 pm (International Centre Diffraction Data (2001), Powder Diffraction File, ICCD, Newtown Square, Paq.), respectively. Furthermore, both copper and iron were encountered in EDS spectra acquired from the regions containing the nanoparticles. Centered DF imaging demonstrated that the diffraction maxima in these patterns originated from the nanoparticles. When viewed in BF, the metallic nanoparticles were very difficult to distinguish from the amorphous background in most regions of the samples. Hence, such particles could easily have been overlooked in the BF imaging techniques used conventionally for biological electron microscopy.

The observed crystallography of non-clumped nanoparticles was that of metallic iron and copper, rather than of salts of these metals. Furthermore, the diffraction patterns encountered in this work were not produced by an organometallic structure. The production of even nanometer-sized metallic particles implies the assembly of a significant number of metal atoms. For example, a 1 nm diameter Cu particle has the same volume as around 10 Cu, or 20 α-Fe, unit cells. FCC metals have 4 atoms per unit cell and BCC metals 2 atoms per cell, indicating a particle containing around 40 atoms in both cases (similarly, a 3 nm diameter particle would contain over 1,000 atoms).

Individual metallic nanoparticles had a random crystallographic orientation. Thus, in cases where the particles had become clumped (in some cases, this appeared to involve flocculation, in others some of the particles had sintered together), a polycrystalline aggregate was produced. In contrast, within a number of relatively large (around 10 nm diameter or above) clumps of particles, significant (~5-10 nm wide) regions were encountered with a constant crystallographic orientation. However, none of the clumps was a true single crystal. Some of these relatively large clumps contained a number of, as yet unidentified, second phases in addition to α-Fe and Cu.

Both Cu and Fe form stable oxides (for example the Gibbs free energy of formation of even the relatively low stability CuO phase is around $-127$ kJ mol$^{-1}$ at 300 K). See Brandes, and Brook (1992) *Smithells Metals Reference Book* (7$^{th}$ ed., Butterworth-Heinenmann, Oxford, UK). Furthermore, the initial stages of oxidation of these metals are rapid, even at room temperature. For example, logarithmic oxidation of initially bare iron, at an oxygen partial pressure of only 10 mPa, results in the growth of around 2 nm of oxide, after less than 20 minutes at 300 K. See Kruger, J. and Yolken (1964), cited by Lawless. (1974) *Rep. Prog. Phys.* 37(2):231-316. The presence of non-noble metallic nanoparticles implies that the surrounding organic matrix has either impeded oxygen access to the metallic particles and/or has a significant reducing effect.

Many of the nanoparticles survived coarsening. The surface energy of the particles provides a driving force for larger particles to cannibalize smaller particles (the surface area to volume ratio for a 1-nm particle is $6 \times 10^9$ m$^{-1}$ and this drops by an order of magnitude for a 10-nm particle). Metallic materials have relatively high solid-vapor interfacial energies ($\gamma_{SV}$) and those for copper and α-iron are around the middle of the range for metallic materials (at ~2.2 and 3.2 J m$^{-2}$, respectively; Murr (1975) *Interfacial Phenomena in Metals and Alloys* (Addison-Wesley; reprinted by TechBooks, Herdon, Va.)). Thus unless the metal-organic matrix interface has an interfacial energy ($\gamma_{SM}$) that is such that $\gamma_{SM} \ll \gamma_{SV}$, there would remain a significant thermodynamic driving force for coarsening. Given the kinetics of coarsening, if all that were present were the metallic nanoparticles, room-temperature coarsening would occur at a negligible rate (solid-state sintering involves bulk diffusion, interfacial diffusion, free surface diffusion and evaporation and re-condensation, all of which would be very slow for Cu or α-Fe at room temperature). See Ashby (1974), *Acta Metallurgica* 22(3):275-289. See also, Swinkels and Ashby (1981) *Acta Metallurgica* 29(2):259-281. Although the presence of the organic liquid matrix raises possibilities for mass transport, it appears that the matrix did not provide a path for the rapid transfer of metal atoms since many of the nanoparticles of served in the present work remained extremely fine.

Example 7

In Vitro Effect of PNC on Cultured Cells

The impact of PNCs upon viability of various cultured cells was investigated using the tetrazolium salt (MTT) cell proliferation assay. RG2 (mouse brain glioma), F98 (rat brain glioma), Hs683 (human brain glioma), CTX TNA2 (rat transfected astrocyte), H9c2[2-1] (rat heart myocardium), 27FR (rat skin fibroblast), and SVGp12 (human brain astroglia) cells were obtained from American Type Culture Collection (ATCC™) and maintained as recommended by ATCC™. MTT cell proliferation assays are commercially available. See, e.g., MTT Cell Proliferation Assay from ATCC™.

Cells were plated in DMEM (Product No. D5648, Sigma)+10% FCS (HyClone) in polystyrene 96-well plates at a density $3\times10^3$ cells per well. Twenty-four hours after plating, the medium was replaced with DMEM with either staurosporine (100 µl, 1 µM) or PNC (aliquots, 100 µl, $5\times10^9$-$3\times10^{11}$ PNC/ml). PNCs were isolated from blood obtained from shark, dog, and rabbit using the ultrafiltration protocol described in Example 5. PNCs were autoclaved at 120° C. and 20 psi for 15 minutes before adding to the cell cultures.

After 20 hours of treatment, a 20-µl aliquot of tetrazolium salt (MTT, 5 mg/ml in PBS) was added to the wells, and interaction was allowed to proceed for 4 hours at 37° C. MTT was reduced in metabolically active cells to form purple formazan crystals, which were dissolved by DMSO and quantified by a plate reader (BioRad). For each cell type, a linear relationship between cell number and absorbance is established, enabling accurate, straightforward quantification of changes in proliferation.

In two trials, the effect of PNCs on RG2 cells was studied utilizing the following protocol:

Day 1. Plate out RG2 cells at a density of $3\times10^3$ cells/well in D5648+10% FCS and incubate overnight.

Staurosporine (Sigma S5921), 100 µg, FW 466.5. Dissolve 100 µg staurosporine into 214.3 µl DMSO to equal a 1 mM stock solution. Store at −200° C. Dilute stock 1:10 in media to equal 0.1 mM or 100 µM stock.

Dilute as follows:

466.5 gm/1 liter 1 M 100 gm/0.214 L=1M

Dilute stock 1:10 10 µl stock+90 µl DMEM

100 µg/2.143 ml=100 µM (frozen stock)

use 10 µl/well=1 µM

Day 2. Remove media and add DMEM+1% FCS (100 µl/well). TX put on late afternoon.

Add staurosporine, autoclaved shark PNC, and either 10%, 1%, or 0% FCS treatments to cells and incubate overnight.

The results of this study are shown in Tables 7 and 8, below. (Ab. Av.=Absorbance at 550 nm; St. Dv.=Standard Deviation)

TABLE 7

MTT assay on RG2 glioma cells, with 10%, 1% and 0% FCS

| | Shark Seeds--autoclaved | | | | | | | |
|---|---|---|---|---|---|---|---|---|
| Shark 3 | 10% FCS no tx | 10% FCS 20 µl | 10% FCS 10 µl | 10% FCS 1 µl | 1% FCS no tx | 1% FCS 20 µl | 1% FCS 10 µl | 1% FCS 1 µl |
| | 0.533 | 0.298 | 0.404 | 0.482 | 0.731 | 0.408 | 0.496 | 0.707 |
| | 0.542 | 0.316 | 0.414 | 0.465 | 0.753 | 0.433 | 0.544 | 0.724 |
| | 0.577 | 0.374 | 0.425 | 0.526 | 0.74 | 0.394 | 0.533 | 0.605 |
| | 0.516 | 0.369 | 0.409 | 0.467 | 0.633 | 0.365 | 0.596 | 0.633 |
| | 0.5 | 0.321 | 0.431 | 0.466 | 0.684 | 0.411 | 0.571 | 0.612 |
| | | 0.362 | 0.414 | | 0.693 | 0.419 | 0.541 | |
| | | 0.285 | 0.373 | | 0.636 | 0.384 | 0.573 | |
| | | 0.297 | 0.393 | | 0.637 | 0.431 | 0.529 | |
| Ab. Av | 0.5336 | 0.32775 | 0.407875 | 0.4812 | 0.688375 | 0.405625 | 0.547875 | 0.6562 |
| St. Dv. | 0.029126 | 0.035568 | 0.018349 | 0.025994 | 0.049494 | 0.023482 | 0.031197 | 0.055432 |

| | Shark Seeds--autoclaved | | | | staurosporine | 10% | 1% | 0% |
|---|---|---|---|---|---|---|---|---|
| Shark 3 | 0% FCS no tx | 0% FCS 20 µl | 0% FCS 10 µl | 0% FCS 1 µl | 10% FCS 1 µM | FCS water 20 µl | FCS water 20 µl | FCS water 20 µl |
| | 0.866 | 0.432 | 0.739 | 0.827 | 0.406 | 0.436 | 0.726 | 0.971 |
| | 0.891 | 0.464 | 0.653 | 0.895 | 0.411 | 0.462 | 0.701 | 0.74 |
| | 0.695 | 0.463 | 0.713 | 0.918 | 0.399 | 0.394 | 0.676 | 0.79 |
| | 0.937 | 0.429 | 0.618 | 0.833 | | | | |
| | 0.799 | 0.463 | 0.638 | 0.78 | | | | |
| | 0.909 | 0.479 | 0.677 | | | | | |
| | 0.928 | 0.452 | 0.577 | | | | | |
| | 0.949 | 0.551 | 0.574 | | | | | |
| Ab. Av | 0.87175 | 0.466625 | 0.648625 | 0.8506 | 0.405333 | 0.430667 | 0.701 | 0.833667 |
| St. Dv. | 0.085951 | 0.038049 | 0.059625 | 0.055599 | 0.006028 | 0.034312 | 0.025 | 0.121533 |

TABLE 8

MTT assay, RG2 cells in 1% FCS, with shark, rabbit and dogs 1 and 2 seeds, autoclaved.

|  | no tx | 20 μl | 10 μl Shark Seeds | 1 μl | 20 μl | 10 μl Dog 1 seeds | 1 μl |
|---|---|---|---|---|---|---|---|
|  | 0.64 | 0.342 | 0.447 | 0.664 | 0.675 | 0.773 | 0.658 |
|  | 0.694 | 0.344 | 0.616 | 0.596 | 0.633 | 0.705 | 0.598 |
|  | 0.667 | 0.373 | 0.407 | 0.595 | 0.527 | 0.662 | 0.712 |
|  | 0.678 | 0.322 | 0.499 | 0.676 | 0.57 | 0.613 | 0.625 |
|  | 0.675 |  |  | 0.626 | 0.63 | 0.63 | 0.625 |
|  |  |  |  | 0.634 | 0.728 | 0.675 | 0.639 |
|  |  |  |  | 0.689 | 0.6 | 0.703 | 0.688 |
|  |  |  |  | 0.596 | 0.719 | 0.629 | 0.61 |
| Ab Av. | 0.6708 | 0.34525 | 0.49225 | 0.6345 | 0.63525 | 0.67375 | 0.644375 |
| St. Dv. | 0.019817 | 0.020998016 | 0.090691326 | 0.038097619 | 0.07015035 | 0.05268437 | 0.03923168 |

|  | 20 μl | 10 μl Dog 2 seeds | 1 μl | 20 μl | 10 μl Rabbit seeds | 1 μl | stauro 1% FCS |
|---|---|---|---|---|---|---|---|
|  | 0.555 | 0.595 | 0.687 | 0.503 | 0.62 | 0.732 | 0.108 |
|  | 0.568 | 0.642 | 0.541 | 0.582 | 0.577 | 0.676 | 0.095 |
|  | 0.543 | 0.65 | 0.601 | 0.476 | 0.607 | 0.589 | 0.093 |
|  | 0.529 | 0.648 | 0.534 | 0.512 | 0.6 | 0.647 |  |
|  | 0.561 | 0.53 | 0.66 | 0.585 | 0.564 | 0.64 |  |
|  | 0.526 | 0.638 | 0.623 | 0.584 | 0.604 | 0.61 |  |
|  | 0.498 | 0.593 | 0.644 | 0.565 | 0.519 | 0.634 |  |
|  | 0.566 | 0.658 | 0.559 | 0.536 | 0.554 | 0.649 |  |
| Ab Av. | 0.54325 | 0.61925 | 0.606125 | 0.542875 | 0.580625 | 0.647125 | 0.09866667 |
| St. Dv. | 0.024294326 | 0.04372887 | 0.05713752 | 0.0423402 | 0.03372976 | 0.0431292 | 0.00814453 |

Similar studies were carried out comparing the effect of shark PNCs with staurosporine. See Tables 9-12, below. A significant decrease in cell viability was observed for cultured cells incubated with PNCs for 20 hours (FIG. 4A). The viability of the rat and mouse glioma cells declined by 90% and 75%, respectively, while the viability of the rat astrocytes decreased by only 25% at the same conditions. Post-exposure morphological observations of cells under optical dark-field microscope showed signs of cell death. Cells were shrunken and rounded; nuclei were condensed and showed budding of cell bodies (FIG. 4B-2). Cell damage produced by the shark PNCs compares well with the injury made by 1 μM of staurosporine (a potent apoptosis-inducing reagent) (FIG. 4B-3). A significant effect on cell viability was also observed with Hs683 (human brain glioma), H9c2[2-1] (rat heart myocardium), 27FR (rat skin fibroblast), and SVGp12 (human brain astroglia) cells. Proteons and PNCs obtained from the blood plasma of healthy dog and rabbit also significantly affected the viability of the cultured mammalian cells.

FIG. 4C shows the viability of RG2 glioma cells exposed to PNCs from different sources. It takes about $1 \times 10^{12}$ PNC/ml to fully suppress these glioma cells. This concentration accounts for not more than 10% of the full concentration of PNCs in a healthy animal.

TABLE 9

MTT assay on various cell lines with shark seeds and 0% FCS

|  |  | RG2 | | | | Fibroblast | | | | Myocard | | |
|---|---|---|---|---|---|---|---|---|---|---|---|---|
|  |  | No tx | 1 μl | 10 μl | 20 μl | No tx | 1 μl | 10 μl | 20 μl | No tx | 1 μl | 10 μl | 20 μl |
| Plate 1 |  | 1.075 | 0.964 | 0.856 | 0.597 | 0.658 | 0.503 | 0.595 | 0.342 | 0.509 | 0.452 | 0.496 | 0.376 |
| 0% FCS |  | 1.169 | 1.014 | 0.791 | 0.496 | 0.603 | 0.517 | 0.541 | 0.36 | 0.462 | 0.373 | 0.471 | 0.382 |
|  |  | 1.103 | 1.016 | 0.688 | 0.523 | 0.558 | 0.556 | 0.492 | 0.375 | 0.494 | 0.438 | 0.462 | 0.33 |
|  |  | 1.084 | 1.082 | 0.739 | 0.55 | 0.556 | 0.569 | 0.432 | 0.382 | 0.449 | 0.446 | 0.513 | 0.309 |
| Ab. Av. |  | 1.10775 | 1.019 | 0.7685 | 0.5415 | 0.59375 | 0.53625 | 0.515 | 0.36475 | 0.4785 | 0.42725 | 0.4855 | 0.34925 |
| St. Dv. |  | 0.042469 | 0.048401 | 0.07191 | 0.04307 | 0.048016 | 0.031298 | 0.069508 | 0.017727 | 0.027767 | 0.036619 | 0.023302 | 0.035491 |

|  |  | CTX astrocytes | | | | SVG astrocytes | | | | F98 glioma | | |
|---|---|---|---|---|---|---|---|---|---|---|---|---|
|  |  | No tx | 1 μl | 10 μl | 20 μl | No tx | 1 μl | 10 μl | 20 μl | No tx | 1 μl | 10 μl | 20 μl |
| Plate 1 |  | 0.622 | 0.596 | 0.555 | 0.429 | 0.678 | 0.688 | 0.441 | 0.275 | 1.045 | 0.914 | 0.367 | 0.213 |
| 0% FCS |  | 0.603 | 0.589 | 0.559 | 0.489 | 0.681 | 0.585 | 0.439 | 0.275 | 0.977 | 0.697 | 0.444 | 0.16 |
|  |  | 0.59 | 0.645 | 0.561 | 0.396 | 0.676 | 0.587 | 0.462 | 0.251 | 0.966 | 0.643 | 0.415 | 0.196 |
|  |  | 0.565 | 0.6 | 0.533 | 0.434 | 0.656 | 0.667 | 0.363 | 0.244 | 1.064 | 0.73 | 0.504 | 0.172 |

TABLE 9-continued

MTT assay on various cell lines with shark seeds and 0% FCS

| | | | | | | | | | | | | |
|---|---|---|---|---|---|---|---|---|---|---|---|---|
| Ab. Av. | 0.595 | 0.6075 | 0.552 | 0.42725 | 0.67275 | 0.63175 | 0.42625 | 0.26125 | 1.013 | 0.746 | 0.4325 | 0.18525 |
| St. Dv. | 0.02393 | 0.02541 | 0.01291 | 0.038549 | 0.011354 | 0.053525 | 0.043431 | 0.016132 | 0.048751 | 0.117601 | 0.057274 | 0.023796 |

TABLE 10

MTT assay on various cell lines with shark seeds and 1% FCS

| Plate 2 | RG2 | | | | Fibroblast | | | |
|---|---|---|---|---|---|---|---|---|
| | No tx | 1 μl | 10 μl | 20 μl | No tx | 1 μl | 10 μl | 20 μl |
| 1% FCS | 0.839 | 0.606 | 0.536 | 0.36 | 0.503 | 0.44 | 0.5 | 0.307 |
| | 0.734 | 0.551 | 0.723 | 0.419 | 0.475 | 0.452 | 0.44 | 0.316 |
| | 0.665 | 0.595 | 0.551 | 0.435 | 0.465 | 0.518 | 0.351 | 0.298 |
| | 0.723 | 0.656 | 0.564 | 0.445 | 0.457 | 0.547 | 0.308 | 0.371 |
| AbAv | 0.74025 | 0.602 | 0.5935 | 0.41475 | 0.475 | 0.48925 | 0.39975 | 0.323 |
| St Dv | 0.072459 | 0.043135 | 0.087088 | 0.038038 | 0.020067 | 0.051558 | 0.086535 | 0.032833 |

| Plate 2 | Myocard | | | | CTX astrocytes | | | |
|---|---|---|---|---|---|---|---|---|
| | No tx | 1 μl | 10 μl | 20 μl | No tx | 1 μl | 10 μl | 20 μl |
| 1% FCS | 0.404 | 0.43 | 0.317 | 0.317 | 0.521 | 0.501 | 0.501 | 0.355 |
| | 0.43 | 0.444 | 0.349 | 0.326 | 0.507 | 0.564 | 0.426 | 0.415 |
| | 0.408 | 0.466 | 0.326 | 0.289 | 0.542 | 0.562 | 0.42 | 0.387 |
| | 0.425 | 0.458 | 0.321 | 0.377 | 0.538 | 0.641 | 0.439 | 0.471 |
| AbAv | 0.41675 | 0.4495 | 0.32825 | 0.32725 | 0.527 | 0.567 | 0.4465 | 0.407 |
| St Dv | 0.012685 | 0.015864 | 0.014315 | 0.036719 | 0.016145 | 0.057347 | 0.037189 | 0.049207 |

| Plate 2 | SVG astrocytes | | | | F98 glioma | | | |
|---|---|---|---|---|---|---|---|---|
| | No tx | 1 μl | 10 μl | 20 μl | No tx | 1 μl | 10 μl | 20 μl |
| 1% FCS | 0.602 | 0.509 | 0.352 | 0.248 | 0.746 | 0.687 | 0.376 | 0.137 |
| | 0.597 | 0.496 | 0.37 | 0.238 | 0.971 | 0.524 | 0.334 | 0.154 |
| | 0.534 | 0.488 | 0.401 | 0.246 | 0.91 | 1.267 | 0.283 | 0.141 |
| | 0.48 | 0.547 | 0.394 | 0.26 | 0.864 | 0.521 | 0.309 | 0.139 |
| AbAv | 0.55325 | 0.51 | 0.37925 | 0.248 | 0.87275 | 0.74975 | 0.3255 | 0.14275 |
| St Dv | 0.057812 | 0.026141 | 0.0225 | 0.009092 | 0.095189 | 0.353447 | 0.039585 | 0.007676 |

TABLE 10

MTT assay on various cell lines with shark seeds and 1% FCS

| | RG2 | | | | Fibroblast | | | | Myocard | | | |
|---|---|---|---|---|---|---|---|---|---|---|---|---|
| St Dv | 0.072459 | 0.043135 | 0.087088 | 0.038038 | 0.020067 | 0.051558 | 0.086535 | 0.032833 | 0.012685 | 0.015864 | 0.014315 | 0.036719 |

| | CTX astrocytes | | | | SVG astrocytes | | | | F98 glioma | | | |
|---|---|---|---|---|---|---|---|---|---|---|---|---|
| St Dv | 0.016145 | 0.057347 | 0.037189 | 0.049207 | 0.057812 | 0.026141 | 0.0225 | 0.009092 | 0.095189 | 0.353447 | 0.039585 | 0.007676 |

TABLE 11

MTT assay on various cell lines with Staurosporine

| Saurosp. | RG2 100 nm | RG2 | Fibro | Fibro | Myocard | myocard | CTX astro |
|---|---|---|---|---|---|---|---|
| Shark 7 | 0.305 | 0.12 | 0.257 | 0.168 | 0.402 | 0.154 | 0.252 |
|  | 0.301 | 0.119 | 0.275 | 0.166 | 0.373 | 0.151 | 0.518 |
| Plate 3 | 0.279 | 0.119 | 0.275 | 0.171 | 0.172 | 0.159 | 0.533 |
| 1% FCS | 0.272 | 0.149 | 0.296 | 0.171 | 0.185 | 0.176 | 0.21 |
| Ab. Av. | 0.28925 | 0.12675 | 0.27575 | 0.169 | 0.283 | 0.16 | 0.37825 |
| St. Dv. | 0.016215 | 0.014841 | 0.015945 | 0.002449 | 0.121362 | 0.011165 | 0.171002 |

| Saurosp. | CTX astro | SVG astro | SVG astro | F98 glioma | F98 glioma |
|---|---|---|---|---|---|
| Shark 7 | 0.212 | 0.128 | 0.067 | 0.136 | 0.108 |
|  | 0.122 | 0.12 | 0.066 | 0.138 | 0.108 |
| Plate 3 | 0.118 | 0.128 | 0.067 | 0.12 | 0.109 |
| 1% FCS | 0.126 | 0.136 | 0.068 | 0.139 | 0.109 |
| Ab. Av. | 0.1445 | 0.128 | 0.067 | 0.13325 | 0.1085 |
| St. Dv. | 0.045118 | 0.006532 | 0.000816 | 0.008921 | 0.000577 |

TABLE 12

Effect of shark extracts on cultured cells as a percentage of metabolically active cells

| | METABOLICALLY ACTIVE CELLS, % | | | |
|---|---|---|---|---|
| CELL LINES (RAT) | Shark extract 1 µl | Shark extract 10 µl | Shark extract 20 µl | Staurosporine 1 µM |
| F98 glioma | 73.6 ± 20.5 | 42.6 ± 18 | 18.2 ± 17.6 | 12.4 ± 11.4 |
| RG2 glioma | 91.9 ± 8.5 | 69.3 ± 13.1 | 48.8 ± 11.7 | 17.1 ± 21.4 |
| Myocardium | 89.2 ± 14.4 | 101.4 ± 10.6 | 72.9 ± 15.9 | 38.3 ± 10 |
| CTX astrocytes | 102.1 ± 8.2 | 92.7 ± 6.3 | 71.8 ± 13.0 | 27.4 ± 34.2 |
| Fibroblasts | 90.3 ± 13.9 | 86.7 ± 21.5 | 61.4 ± 12.9 | 35.5 ± 5.6 |
| SVG astrocytes | 93.9 ± 10.1 | 63.3 ± 11.8 | 38.8 ± 7.8 | 12.1 ± 11.6 |

Example 8

Cyclic Amplification of Proteons

A progressively increased number of proteons can be produced from plasma subjected to increasing temperatures. To examine a method of cyclic amplification, seven 1 ml samples of plasma were prepared for cyclic amplification. After the initial number of proteons was quantitated by a dark-field microscope, the first sample was incubated for 15 minutes at 65° C. and normal pressure. Five µl of the treated first sample was introduced to seed the untreated second sample, and the second sample was incubated for 15 minutes at 65° C. and normal pressure. This step was repeated: 5 µl of the second amplified sample was added to the third untreated sample. This process was repeated up to 6 cycles. A control series was run by adding of five µl of purified water (instead of seeds) to 1 ml of untreated plasma.

The first two cycles resulted in a small but significant ($p<0.001$) increase of proteon population, whereas the third cycle brought about a dramatic increase in the number of proteons. The next three cycles resulted in saturation of the proteon population. In contrast, the control samples showed no dramatic increase of the proteon population. See FIG. 2.

Example 9

Comparison With Other Biological Particles

Experiments were carried out to compare the proteons obtained by the procedure described in the Example 1 with the nanobacteria isolated from blood by Kajander et al. (1996) *Mol. Biol. Cell* 7:3007-3007 using the NANOCAPTURE ELISA™, an Enzyme-Linked Immunosorbent Assay, for detection of nanobacterial antigens (Nanobac OY, Finland). The nanobacteria included in the Nanocapture ELISA were used as a positive control. The Microplate Manager 4.01 Bio-Rad was used to obtain the results of the ELISA. The assay procedure was carried out following the manufacturer's recommendations. The reaction was considered to be positive when the absorbance was significantly higher then the level of noise. Results of interaction of antibodies grown against nanobacteria with proteons and plasma are summarized in Table 13.

TABLE 13

Interaction of antibodies specific to nanobacteria with proteons and plasma.

| No | Sample | Condition | Reaction |
|----|--------|-----------|----------|
| 1 | Proteons, human 1 | Freshly prepared at 120° C. and 20 psi, 2 h | − |
| 2 | Proteons, human 2 | Freshly prepared at 120° C. and 20 psi, 2 h | − |
| 3 | Proteons, rabbit | Freshly prepared at 120° C. and 20 psi, 2 h | − |
| 4 | Proteons, human 1 | Incubated 13 days, 37° C. after preparation | − |
| 5 | Plasma, human | Freshly prepared | − |
| 6 | Plasma, human 1 | Incubated 13 days, 37° C. | − |
| 7 | Proteons, human 1, in D5648[a] | Incubated 13 days, 37° C. | + |
| 8 | Proteons human 1, in D6429[b] | Incubated 13 days, 37° C. | + |
| 9 | Plasma, human 1, in D5648[a] | Incubated 13 days, 37° C. | + |
| 10 | Plasma, human 1, in D6429[b] | Incubated 13 days, 37° C. | + |
| 11 | Proteons, human 1, in D5648[a] | Incubated 13 days, 37° C. | + |
| 12 | Proteons, human 1, in D6429[b] | Incubated 13 days, 37° C.; 5% $CO_2$-95% air | + |
| 13 | Plasma, human 1, in D5648[a] | Incubated 13 days, 37° C.; 5% $CO_2$-95% air | + |
| 14 | Plasma, human 1, in D6429[b] | Incubated 13 days, 37° C.; 5% $CO_2$-95% air | + |
| 15 | Proteons, human 1, in D5648[a] | Incubated 13 days, 37° C.; 5% $CO_2$-95% air | + |
|  | D5648[a] | Incubated 13 days, 37° C. | + |
|  | D6429[b] | Incubated 13 days, 37° C. | + |
| 16 | D6429[b] | Freshly prepared | − |
| 17 | Water[c] | Freshly prepared | − |
| 18 | Broth[d] | 120° C. and 20 psi, 2 h | − |
|  | Nanobacteria |  | + |

[a]D5648 tissue culture media (Sigma) with 10% FBS (HyClone).
[b]D6429 tissue culture media (Sigma) with 10% FBS (HyClone).
[c]Purified water (Direct QTM, Millipore, 17 MOhm)
[d]LB-Medium (BIO 101, Inc.; 10 g Trypton-B, 5 g yeast extract-B, 10 h NaCl in 1 L of water).

Nanobacteria gave a positive signal, while all freshly prepared proteons showed no interaction. Proteons incubated in cell culture media for 13 days, at 37° C. (with and without $CO_2$) show a positive reaction. However, the culture media alone incubated for 13 days, at 37° C. also gave a positive reaction, while freshly prepared culture media was negative, indicating that nanobacteria antigen appeared from the culture media during the incubation.

Example 10

Methods of Shark PNC preparation

A) Shark Blood

Fresh blue shark (Prionace) tissue was homogenized in purified water (1:1, w/w) and suspension was centrifuged at 12,800×g for 40 minutes at 4° C. The final filtrate was obtained by filtering the supernatant consecutively through 30-kDa and 5-kDa CENTRICON™ filters (Millipore). Liquid obtained by filtration was autoclaved at 20 psi for 15 minutes. Micrometer and sub-micrometer particles were isolated from shark extracts. It was initially observed that shark's blood contains approximately 5-fold more PNCs/ml than rat or rabbit blood. Specifically, one microliter of shark extract contained approximately $5 \times 10^{13}$ proteon nucleating centers (PNC). PNCs such as these are generally comprised of 1-2-nm metallic nanoclusters containing 40-300 atoms.

B) Shark liver.

The shark's body and liver were stored in ice for approximately 12 h. The tissue was homogenized using various methods. Specifically, 50 g of liver was homogenized in 150 ml $H_2O$ (DIRECT-Q™ water purification system, Millipore) in a blender. Additionally, 50 g of liver was homogenized in 150 ml of 0.2% NaCl/$H_2O$ solution in a blender, and 50 g of liver was also homogenized in 150 ml of 0.9% NaCl and 0.9% Ethanol solution. Blood was diluted approximately 1:10 in water.

The homogenates were centrifuged at 12,800 g-13,000 g for 40 min. on a Beckman (Model J2-21™) centrifuge in a JA 10™ rotor. The pellet was discarded and the supernatant was filtered through 30,000 Da CENTRICON PLUS-80™ centrifugal filter devices (Millipore). Samples were combined and filtered through a 5,000 Da CENTRICON PLUS-80™ centrifugal filter device, yielding a PNC "seed solution."

1) PNC Formation for Metal Analysis (From "Seed solution")

450 mg of $MgSO_4 \times 7H_2O$ was added to approximately 150 ml shark seed solution having a pH approximately 6-7. 1N NaOH was added to the solution to raise pH to 11, approximately. White precipitate was formed, and the precipitate was centrifuged at 5000 rpm on a Beckman table centrifuge. Supernatant was discarded and the pellet was dissolved by lowering the pH to between 6-7 using a 1N solution of HCl. Analysis showed the presence of Zn, Cu and Mg in the solution.

2) PNC Formation for Cell Culture (From "Seed Solution")

20 ml of the "seed solution was autoclaved for 15 minutes at 20 psi and used for cultured cell experiments.

C) Rabbit Blood

Plasma was obtained by adding 10 ml of rabbit blood to 290 ml $H_2O$ (DIRECT-Q™ water purification system, Millipore) (1:30). The solution was mixed and centrifuged for 40 min at 13,000 g on a Beckman (Model J2-21™) centrifuge in a JA 10™ rotor. The pellet was discarded and the supernatant was used for seed preparation. PNC were obtained by filtering plasma through 30,000 Da and then 5,000 Da CENTRICON PLUS-80™ centrifugal filter devices (Millipore).

Further preparation for electron microscopy of some samples included adding $MgSO_4 \times 7H_2O$ (Humco) to the PNC suspension ($MgSO_4 \times 7H_2O$+360 ml of seeds solution, pH approximately 5-6). As series of precipitation were performed as follows $1^{st}$ precipitation. (Sample A). The pH of the seed solution was changed to 7 approximately by adding 1N NaOH. A white deposit was formed. The deposit was taken from the solution by pipetting and deposited on a 400 mesh nickel TEM grid. Then the rest of the sample was centrifuged at 5000 rpm on a Beckman-Coulter Allegra™ 21R centrifuge in a S4180™ bucket rotor for 15 min.

2nd precipitation. (Sample B). The pH of the remaining PNC suspension was changed from 7 to 8 by adding 1N NaOH. A white deposit was again formed. The deposit was taken from the solution by pipetting and deposited on a 400 mesh nickel TEM grid. Then the rest of the sample was centrifuged at 5000 rpm on a Beckman-Coulter Allegra™ 21R centrifuge in a S4180™ bucket rotor for 15 min.

3rd precipitation. (Sample C). The pH of the remaining PNC suspension was changed from 8 to 12 by adding 1N NaOH. A white deposit was again formed. The deposit was taken from the solution by pipetting and deposited on a 400 mesh nickel TEM grid. Then the rest of the sample was centrifuged at 5000 rpm on a Beckman-Coulter Allegra™ 21R centrifuge in a S4180™ bucket rotor for 15 min.

D) Mammalian Blood: Rabbit, Dog, and Human

1. Rabbit blood, dog blood, and human blood were each diluted in $H_2O$ (DIRECT-Q™ water purification system, Millipore). Specifically, 25 ml of rabbit blood was diluted in 150 ml of water; 10 ml of dog blood was diluted in 150 ml water; and 60 μl of human blood was diluted in 0.97 ml of $H_2O$. Rabbit and dog plasma were centrifuged at 12,800-13,000 g for 40 min on a Beckman (Model J2-21™) centrifuge in a JA 10™ rotor. The pellet was discarded and the supernatant was used for PNC preparation. Human plasma was centrifuged at 6,500 rpm for 5 min on table centrifuge. The pellet was discarded and the supernatant was used for PNC preparation.

PNC were obtained by sequentially filtering the supernatants though 30,000 Da and 5,000 Da CENTRICON PLUS-80™ centrifugal filter devices (Millipore). The filtered PNC suspensions (2 ml) were autoclaved in 4 ml bottles for 15 min at 20 psi and used for cultured cells experiments.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

The invention claimed is:

1. A process for isolating proteon nucleation centers (PNCs), the process comprising:
    a) centrifuging a biological sample comprising PNCs until a supernatant is formed,
    wherein said PNCs comprise metallic nanoparticles and wherein the biological sample is blood or plasma;
    b) filtering the supernatant through a 5 kDa nominal molecular weight limit ultrafiltration membrane;
    c) collecting a filtrate; and
    d) isolating the PNCs from the filtrate.

2. A process for preparing isolated proteon nucleation centers (PNCs), the process comprising:
    a) centrifuging a biological sample comprising PNCs until a supernatant is formed, wherein the biological sample is a biological sample obtained from an animal;
    b) filtering the supernatant through a filter that retains molecules having a molecular weight of at least 5 kDa;
    c) collecting a filtrate; and
    d) isolating the PNCs from the filtrate.

3. The process of claim 2, wherein centrifuging comprises applying a relative centrifugal force of at least 12,000×g.

4. The process of claim 2, wherein the biological sample is a mammalian biological sample.

5. The process of claim 4, wherein the mammalian biological sample is blood or plasma.

6. The process of claim 4, wherein the mammalian biological sample is human blood or human plasma.

7. The process of claim 2, wherein prior to filtering the supernatant through a filter that retains molecules having a molecular weight of at least 5 kDa, the supernatant is prefiltered through a filter selected from the group consisting of a 0.5 micron filter, a 0.22 micron filter, a 0.2 micron filter, a 100 kDa nominal molecular weight cutoff filter, a 50 kDa nominal molecular weight cutoff filter, a 30 kDa nominal molecular weight cutoff filter, a filter having a nominal molecular weight cutoff within the range of 5 kDa to 30 kDa, and a combination thereof.

8. The process of claim 2, wherein isolating the PNCs from the filtrate comprises precipitating the PNCs from the filtrate.

9. The process of claim 8, wherein precipitating comprises adding $MgSO_4$ to the filtrate.

10. The process of claim 9, wherein the filtrate has a pH of approximately 6-7, and precipitating further comprises raising the pH of the filtrate.

11. The process of claim 10, wherein raising the pH of the filtrate comprises adding NaOH to the filtrate.

12. The process of claim 10, further comprising dissolving the PNCs in a solution having a pH between 6-7.

13. The process of claim 9, wherein the filtrate has a pH of approximately 5-6, and precipitating further comprises raising the pH of the filtrate.

14. The process of claim 13, wherein raising the pH of the filtrate comprises adding NaOH to the filtrate.

15. The process of claim 2, further comprising:
    e) autoclaving the isolated PNCs.

16. The process of claim 2, further comprising:
    e) increasing concentration of the PNCs by evaporation.

17. The process of claim 2, wherein the isolated PNCs prepared by the process have a concentration of greater than about $5 \times 10^{13}$ PNC/ml.

18. A process for preparing isolated proteon nucleation centers (PNCs), the process comprising:
    a) Centrifuging plasma comprising PNCs until a supernatant is formed;
    b) filtering the supernatant through a filter that retains molecules having a molecular weight of at least 5 kDa;
    c) collecting a filtrate;
    d) forming a precipitate from the filtrate; and
    e) dissolving or suspending the precipitate thereby preparing the isolated PNCs.

* * * * *

```
                         SEQUENCE LISTING

<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: Partial Sequence Showing Homology with Rabbit
      Alpha Chain of Hemoglobin
<220> FEATURE:
<221> NAME/KEY: Xaa
<222> LOCATION: (6)..(6)
<223> OTHER INFORMATION: "Xaa" in position #6 is D or E
<220> FEATURE:
<221> NAME/KEY: Xaa
<222> LOCATION: (7)..(7)
<223> OTHER INFORMATION: "Xaa" in position #7 is E or K
<220> FEATURE:
<221> NAME/KEY: Xaa
<222> LOCATION: (10)..(10)
<223> OTHER INFORMATION: "Xaa" in position #10 is A or I

<400> SEQUENCE: 1

Val Leu Ser Pro Ala Xaa Xaa Thr Asn Xaa
1               5                   10
```